(12) United States Patent
Dong et al.

(10) Patent No.: US 9,777,039 B2
(45) Date of Patent: Oct. 3, 2017

(54) SOMATOSTATIN ANALOGS AND DIMERS THEREOF

(71) Applicant: Ipsen Pharma S.A.S., Boulogne-Billancourt (FR)

(72) Inventors: Zheng Xin Dong, Holliston, MA (US); Eric Ferrandis, Saint Remy les Chevreuse (FR)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 192 days.

(21) Appl. No.: 14/439,147

(22) PCT Filed: Oct. 31, 2013

(86) PCT No.: PCT/US2013/067651
§ 371 (c)(1),
(2) Date: Apr. 28, 2015

(87) PCT Pub. No.: WO2014/070965
PCT Pub. Date: May 8, 2014

(65) Prior Publication Data
US 2015/0252078 A1    Sep. 10, 2015

Related U.S. Application Data

(60) Provisional application No. 61/721,449, filed on Nov. 1, 2012.

(51) Int. Cl.
| | | |
|---|---|---|
| *A61K 51/00* | (2006.01) | |
| *A61M 36/14* | (2006.01) | |
| *C07K 7/64* | (2006.01) | |
| *A61K 38/12* | (2006.01) | |
| *G01N 33/74* | (2006.01) | |

(52) U.S. Cl.
CPC ............... *C07K 7/64* (2013.01); *A61K 38/12* (2013.01); *G01N 33/74* (2013.01); *G01N 2333/726* (2013.01)

(58) Field of Classification Search
CPC .... C07K 7/64; G01N 33/74; G01N 2333/726; A61K 38/00; A61K 38/12
USPC ........ 424/1.11, 1.65, 1.69, 9.1, 9.2, 9.3, 9.4, 424/9.5, 9.6; 514/1, 1.1, 11.1, 21.1, 21.7, 514/21.6, 21.5, 21.4, 19.3, 19.4, 19.5, 514/19.6, 19.7, 19.8, 19.9; 530/300, 311, 530/317, 324, 325, 326, 327, 328
See application file for complete search history.

(56) References Cited

U.S. PATENT DOCUMENTS

| | | | |
|---|---|---|---|
| 2,589,978 A | 3/1952 | Stoll et al. | |
| 2,619,488 A | 11/1952 | Stoll et al. | |
| 3,901,894 A | 8/1975 | Kornfeld et al. | |
| 3,966,941 A | 6/1976 | Semonsky et al. | |
| 4,108,855 A | 8/1978 | Mago nee Karacsony et al. | |
| 4,166,182 A | 8/1979 | Kornfeld et al. | |
| 4,526,892 A | 7/1985 | Salvati et al. | |
| 4,871,717 A | 10/1989 | Coy et al. | |
| 4,904,642 A | 2/1990 | Coy et al. | |
| 5,043,341 A | 8/1991 | Cohen et al. | |
| 5,145,837 A | 9/1992 | Feyen et al. | |
| 5,411,966 A | 5/1995 | Sauer et al. | |
| 5,621,133 A | 4/1997 | DeNinno et al. | |
| 5,707,648 A | 1/1998 | Yiv | |
| 5,753,618 A | 5/1998 | Cavanak et al. | |
| 5,925,618 A | 7/1999 | Baumbach et al. | |
| 6,025,193 A | 2/2000 | Weiss | |
| 6,066,616 A | 5/2000 | Cavanak et al. | |
| 6,117,427 A | 9/2000 | Hill et al. | |
| 6,221,870 B1 | 4/2001 | Pfaeffli et al. | |
| 6,358,967 B1 | 3/2002 | Wyrwa et al. | |
| 6,465,613 B1 | 10/2002 | Coy et al. | |
| 6,468,767 B1 | 10/2002 | Weinshank et al. | |
| 7,101,843 B2 | 9/2006 | Glaesner et al. | |
| 7,517,853 B2 | 4/2009 | Dong et al. | |
| 7,572,883 B2 | 8/2009 | Culler et al. | |
| 7,579,435 B2 | 8/2009 | Culler et al. | |
| 7,897,578 B2 | 3/2011 | Ferrandis et al. | |
| 8,178,651 B2 | 5/2012 | Culler et al. | |
| 8,324,386 B2 | 12/2012 | Culler et al. | |

(Continued)

FOREIGN PATENT DOCUMENTS

| | | |
|---|---|---|
| BE | 618187 | 9/1962 |
| CH | 652720 A5 | 11/1985 |

(Continued)

OTHER PUBLICATIONS

Wick, M. M., Levodopa and Dopamine Analogs: Melanin Precursors as Antitumor Agents in Experimental Human and Murine Leukemia, Cancer Treat Rep., 1979, 63: 991-997.
Yamashita, K. et al., "Inhibitory effect of somatostatin on Helicobacter pylori proliferation in vitro", 1998, Gastroenterology, 115:1123-1130.
Rohrer, Susan P. et al., Rapid Identification of Subtype-Selective Agonists of the Somatostatin Receptor Through Combinatorial Chemistry, Science, 1998, 282:737-740.
Ross, Nathan T. et al., Synthetic Mimetics of Protein Secondary Structure Domains, Phil. Trans. R. Soc., 2010, 368:989-1008.

(Continued)

*Primary Examiner* — D L Jones
(74) *Attorney, Agent, or Firm* — Eileen J. Ennis; Ipsen Bioscience, Inc.

(57) ABSTRACT

The present invention relates to novel somatostatin analogs, dimers thereof, and methods of using the same to treat various diseases. Naturally occurring somatostatins (SSTs), which are also known as somatotropin release-inhibiting factors (SRIFs), have diverse biological effects in many cells and organs 10 throughout the body. They are produced by normal endocrine, gastrointestinal, immune and neuronal cells, as well as by certain tumors (Patel, Y. C, Frontiers in Neuroendocrinology, 20(3): 157-198 (1999); Froidevaux, et al., Biopolymers, 66(3): 161-83 (2002)).

15 Claims, No Drawings

(56) References Cited

U.S. PATENT DOCUMENTS

| | | | |
|---|---|---|---|
| 8,952,128 B2* | 2/2015 | Dong | C07C 215/52 530/311 |
| 9,040,482 B2 | 5/2015 | Cintrat et al. | |
| 2004/0209798 A1 | 10/2004 | Culler et al. | |
| 2005/0042753 A1 | 2/2005 | Yang et al. | |
| 2005/0118099 A1 | 6/2005 | Braslawsky et al. | |
| 2005/0159356 A1 | 7/2005 | Dong et al. | |
| 2005/0222025 A1 | 10/2005 | Culler et al. | |
| 2006/0034937 A1 | 2/2006 | Patel | |
| 2006/0052289 A1 | 3/2006 | Bruns et al. | |
| 2006/0058221 A1 | 3/2006 | Miller | |
| 2006/0211607 A1 | 9/2006 | Culler et al. | |
| 2006/0251726 A1 | 11/2006 | Lin et al. | |
| 2006/0292099 A1 | 12/2006 | Milburn et al. | |
| 2007/0154392 A1 | 7/2007 | Maecke et al. | |
| 2008/0039405 A1 | 2/2008 | Langley et al. | |
| 2011/0064742 A1 | 3/2011 | Vranic et al. | |
| 2011/0065632 A1 | 3/2011 | Dong et al. | |
| 2011/0178013 A1 | 7/2011 | Paternostre et al. | |
| 2012/0010154 A1 | 1/2012 | Dong et al. | |
| 2015/0148522 A1 | 5/2015 | Dong et al. | |
| 2015/0290330 A1 | 10/2015 | Dong et al. | |

FOREIGN PATENT DOCUMENTS

| | | |
|---|---|---|
| DE | 140044 | 2/1980 |
| EP | 0126968 B1 | 12/1988 |
| EP | 1099707 A2 | 5/2011 |
| GB | 359261 | 5/1964 |
| GB | 2103603 A | 2/1983 |
| GB | 2112382 A | 7/1983 |
| WO | 91/11447 A1 | 8/1991 |
| WO | 94/14806 A1 | 7/1994 |
| WO | 94/17104 A1 | 8/1994 |
| WO | 99/22735 A1 | 5/1999 |
| WO | 00/04916 A1 | 2/2000 |
| WO | 01/12155 A1 | 2/2001 |
| WO | 02/10215 A1 | 2/2002 |
| WO | 02/085902 A1 | 10/2002 |
| WO | 03/014158 A1 | 2/2003 |
| WO | 2004/091490 A2 | 10/2004 |
| WO | 2005/058252 A2 | 6/2005 |
| WO | 2005/117830 A1 | 12/2005 |
| WO | 2005/120453 A1 | 12/2005 |
| WO | 2009/139855 A2 | 11/2009 |
| WO | 2011/104627 A1 | 9/2011 |
| WO | 2011115871 A1 | 9/2011 |
| WO | 2014/070971 A2 | 5/2014 |

OTHER PUBLICATIONS

International Search Report and Written Opinion from ISA/US mailed Apr. 30, 2014 for International Application No. PCT/US2013/067651.

International Search Report and Written Opinion from ISA/US mailed May 12, 2014 for International Application No. PCT/US2013/67661.

Andersen, M., The Role of Lanreotide Autogel(R) in the Treatment of Acromegaly, Expert Review of Endo. & Metabolism, 2007, p. 433-441, vol. 2, No. 4, Future Drugs Ltd., GB.

Baragli, et al., "Hetero-oligomerization of dopamine (D2R) and SST receptors (SSTRs) in CHO-K1 cells and cortical cultured neurons," Proc. 85th Endo. Soc. Mtg, Philadelphia, PA, USA, 2003, p. 2-669, Abstract only.

Basu, S. et al., "The neurotransmitter dopamine inhibits angiogenesis induced by vascular permeability factor/vascular endothelial growth factor," Nature Medicine, 2001, 7:569-574.

Basu, S. et al., "Dopamine, a neurotransmitter, influences the immune system," J. of Neuroimmunology, 2000, 102:113-124.

Basu, S. et al., "Role of Dopamine in Malignant Tumor Growth," Endocrine, 2000, 12:237-241.

Bosquet, C. et al., "Antiproliferative Effect of Somatostatin and Analogs," Chemotherapy, 2001, 47:30-39.

Colao, A. et al., "Growth hormone and prolactin excess," The Lancet, 1998, 352:1455-1461.

Culler, M. et al., The somatostatin-dopamine chimeric molecule, BIM-23A760, does not induce the insulin/glycemic effects observed with individual somatostatin or dopamine agonists in cynomolgus monkeys (Macaca fascicularis), 12th Mtg. of the Euro. Neuro. Assoc., Athens, Greece, 2006.

Culler, M. D., "Somatostatin-Dopamine Chimeras: A Novel Approach to Treatment of Neuroendocrine Tumors," Horm. Metab. Res., 2011, 43: 854-857.

Figueroa, F. E. et al., "Bromocriptine induces immunological changes related to disease parameters in rheumatoid arthritis", Br. J. Rheum., 1997, 36:1022-1023.

Fioravanti et al., "Somatostatin 14 and joint inflammation: evidence for intraarticular efficacy of prolonged administration in rheumatoid arthritis", Drugs Exp. Clin. Res., 1995, 21:97-103. (Abstract only).

Florio, T. et al., "Efficacy of a dopamine-somatostatin chimeric molecule, BIM-23A760, in the control of cell growth from primary cultures of human non-functioning pituitary adenomas: a multicenter study," Endocrine-Related Cancer, 2008, 15:583-596.

Freda, P. et al., "Clinical Review 110: Diagnosis and treatment of pituitary tumors," J. Clin. Endo. Metab., 1999, 84(11):3859-3866.

Froidevaux, S. et al., "Somatostatin Analogs and Radiopeptides in Cancer Therapy," Biopolymers, 2002, 66:161-183.

Gabor, F. et al., "Drug-protein conjugates: haptenation of 1-methyl-10a-methozydihydrolysergol and 5-bromonicotinic acid to albumin for the production of epitope-specific monoclonal antibodies against nicergoline", J. Pharm. Sci., 1995, 84:1120-1125.

Goldstein, M. et al., "Dopaminergic mechanisms in the pathogenesis of schizophrenia," FASEB Journal, 1992, 6:2413-2421.

Graybiel, A. et al., "The Nigrostriatal System in Parkinson's Disease," Adv. Neurol., 1990, 53: 17-29.

Hoffman, A.J. et al., "Synthesis and LSD-like Discriminative Stimulus Properties in a Series of N(6)-Alkyl Norlysergic Acid N,N-Diethylamide Derivatives," J. Med. Chem., 1985, 28(9):1252-1255.

Ishibashi, M., et al., "Inhibition of growth of human small cell lung cancer by bromocriptine", Cancer Res., 1994, 54:3442-3446.

Jaquet, P., "Evidence for dopamine agonists in the treatment of acromegaly," J. Endo., 1997, 155:S59-S60.

Jaquet, P. et al., "Quantitative and functional expression of somatostatin receptor subtypes in human prolactinomas," J. Clin. Endo. Metab., 1999, 84(9):3268-3276.

Jaquet, P. et al., "Efficacy of chimeric molecules directed towards multiple somatostatin and dopamine receptors on inhibition of GH and prolactin secretion from GH-secreting pituitary adenomas classified as partially responsive to somatostatin analog therapy", Eu. J. Endo., 2005, 153:135-141.

Jenkinson, D. H. et al., "International Union of Pharmacology Committee on Receptor Nomenclature and Drug Classification. IX. Recommendations on Terms and Symbols in Quantitative Pharmacology," Pharmacol. Rev., 1995, 47(2):255-266.

Krepelka, J. et al., "Some esters of N-(D-6-methyl-8-ergolin-1-ylmethyl)-carbamic acid," Collection Czechoslov. Chem. Commun., 1977, 42:1886-1889.

Losse, G. et al., "Synthese von lysergyl-enkephalin-derivaten," Eur. J. Med. Chem., 1979, 14:325-328.

Maheshwari, H. et al., "Long-acting peptidomimergic control of gigantism caused by pituitary acidophilic stem cell adenoma," J. Clin. Endo. Metab., 2000, 85(9):3409-3416.

Mantegani, S. et al., "Synthesis and antihypertensive activity of 2,4-dioxoimidazolidin-1-yl and perhydro-2,4-dioxopyrimidin-1-yl ergoline derivatives," Il Farmaco, 1998, 53:293-304.

Miyagi, M. et al., "Dopamine receptor affinities in vitro and stereotypic activities in vivo of cabergoline in rats," Biol. Pharm. Bull., 1996, 19:1210-1213.

Nicolaus, B. J. R., "Symbiotic Approach to Drug Design," Decision Making in Drug Research, 1983, 173-186.

Olanow, C. W. et al., "Etiology and Pathogenesis of Parkinson's Disease," Annu. Rev. Neurosci, 1999, 22: 123-144.

Patel, Yogesh C., "Somatostatin and Its Receptor Family," Frontiers in Neuroendocrinology, 1999, 20: 157-198.

(56) References Cited

OTHER PUBLICATIONS

Pfeiffer, M. et al., "Heterodimerization of Somatostatin and Opioid Receptors Cross-modulates Phosphorylation, Internalization, and Densensitization," J. Biol. Chem., 2002, 277: 19762-19772.

Racine, M. et al., "Medical Management of Growth Hormone-Secreting Pituitary Adenomas," Pituitary, 2002, 5: 67-76.

Reisine, T. et al., "Molecular Biology of Somatostatin Receptors," Endo. Rev., 1995, 16: 427-442.

Reubi, J.C. et al., "Distribution of somatostatin receptors in normal and neoplastic human tissues: Recent advances and potential relevance," Yale J. Biol. and Med., 1997, 70:471-479.

Reubi, J. C. et al., "Somatostatin Receptors in Human Endocrine Tumors," Cancer Res., 1987, 47: 551-558.

Rocheville, M. et al., "Receptors for Dopamine and Somatostatin: Formulation of Hetero-Oligomers with Enhanced Functional Activity," Science, 2000, 288(5643):154-157.

Saveanu, A. et al, Demonstration of Enhanced Potency of a Chimeric Somatostatin-Dopamine Molecule, BIM-23A387, in Suppressing Growth Hormone and Prolactin Secretion from Human Pituitary Somatotoph Adenoma Cells, J. of Clinical Endo. & Metabolism, 2002, p. 5545-5552, vol. 87, No. 12, The Endocrine Society, US.

Saveanu, A. et al., "A chimeric somatostatin-dopamine molecule, BIM-23A387 has enhanced potency in suppressing GH and PRL secretion in acromegaly," ENEA 2002 Conference, Munich, Germany, Sep. 12-14, 2002, OC-2.4, p. 49, Abstract (XP-002306950).

Stoll, A. et al., "Synthesis of 6-Methyl-8-oxyisoergoline (I) and Attempts to Dehydrogenate Same to 6-Methyl-ergolin-8-one," 28th Report on Ergot Alkaloids, Helvetica Chimica Acta., 1952, 35(152-153):1249-1258.

Strosberg, J. et al., "Antiproliferative effect of somatostatin analogs in gastroenteropancreatic neuroendocrine tumors," World J. Gastroenterol, 2010, 26: 2963-2970.

Sweet, et al., "Piribedil—an oral dopamine agonist for treatment of Parkinson's disease", Trans. Am. Neurol. Assoc., 1974, 99:258-60. (Title only).

Tangbanluekal, L. et al., "Prolactin mediates estradiol-induced inflammation in the lateral prostate of Wistar rats," Endocrinology, 1993, 132:2407-2416.

Taylor, J. E., et al.,"In vitro and in vivo inhibition of human small cell lung carcinoma (NCI-H69) growth by a somatostatin analogue", Biochem. Biophys. Res. Comm., 1988, 153:81-86.

Temperilli, A. et al., "Anti-hypertensive activity of ergolinyl-ureido and thioureido derivatives", Eur. J. Med. Chem., 1988, 23:77-81.

Terenius, L., "Somatostatin and ACTH are peptides with partial antagonist-like selectivity for opiate receptors", Eur. J. Pharmacol., 1976, 38:211-3. (Abstract only).

Torsello, A. et al., "Short Ghrelin Peptides Neither Displace Ghrelin Binding In Vitro Nor Stimulate GH Release In Vivo," Endo., 2002, 143: 1968-1971.

Walzel, B. et al., "Mechanism of alkaloid cyclopeptide synthesis in the ergot fungus *Claviceps purpurea*," Chemistry and Biology, 1997, 4:223-230.

Wick, M. M. et al., "Dopamine: A Novel Antitumor Agent Active Against B-16 Melanoma In Vivo," J. Investigative Derm., 1978, 71: 163-164.

Wick, M. M., "3,4-Dihydroxybenzylamine: A Dopamine Analog With Enhanced Antitumor Activity Against B16 Melanoma," J. Natl. Cancer Inst., 1979, 63: 1465-1467.

* cited by examiner

SOMATOSTATIN ANALOGS AND DIMERS THEREOF

This application is a United States national stage filing under 35 U.S.C. §371 of international (PCT) application no. PCT/US2013/067651, filed Oct. 31, 2013, and designating the US, which claims priority to U.S. provisional application No. 61/721,449, filed Nov. 1, 2012, each of which is herein incorporated by reference in its entirety.

FIELD OF THE INVENTION

The present invention relates to novel somatostatin analogs, dimers thereof, and methods of using the same to treat various diseases.

BACKGROUND OF THE INVENTION

Naturally occurring somatostatins (SSTs), which are also known as somatotropin release-inhibiting factors (SRIFs), have diverse biological effects in many cells and organs throughout the body. They are produced by normal endocrine, gastrointestinal, immune and neuronal cells, as well as by certain tumors (Patel, Y. C., *Frontiers in Neuroendocrinology*, 20(3): 157-198 (1999); Froidevaux, et al., *Biopolymers*, 66(3): 161-83 (2002)). The effects of somatostatins are broadly inhibitory on the secretion of hormones, as well as on the proliferation and survival of cells. They inhibit both endocrine secretion (e.g., growth hormone, insulin, glucagon, gastrin, cholecystokinin, vasoactive intestinal peptide and secretin) and exocrine secretion (e.g., gastric acid, intestinal fluid and pancreatic enzymes) (Patel, Y. C., (1999) op. cit.). Somatostatins also inhibit proliferation of both normal and tumor cells (Bousquet et al., *Chemotherapy*, 47(2): 30-39 (2001)).

These biological effects of somatostatins, all inhibitory in nature, are elicited through a series of G protein coupled receptors, of which five different subtypes have been characterized (SSTR1-5) (Reubi, et al., *Cancer Res*, 47: 551-558 (1987); Reisine, et al., *Endocrine Review*, 16: 427-442 (1995); Patel, Y. C., (1999) op. cit.)). SSTR1-5 have similar affinities for the endogenous somatostatin ligands but have differing distribution in various tissues.

Somatostatin analogs were initially developed for the control of hormonal syndromes associated with neuroendocrine tumors (NETs). In recent years, accumulating data has supported their role as antiproliferative agents, capable of stabilizing tumor growth in patients with metastatic neuroendocrine malignancies, including carcinoid and pancreatic endocrine tumors (Strosberg, et al., *World J Gastroenterol*, 26(24): 2963-2970 (2010)).

Examples of somatostatin analogs are disclosed in, e.g., PCT publication Nos. WO 02/10215; WO 2007/144492; WO 2010/037930; WO 99/22735; and WO 03/014158.

As is well known to those skilled in the art, SRIF and analogs thereof are useful in the treatment of a great variety of diseases and/or conditions. An exemplary but by no means exhaustive list of such diseases and/or conditions would include: Cushing's syndrome (Clark, R. V. et al., *Clin. Res.*, 38: 943A (1990)); gonadotropinoma (Ambrosi, B. et al., *Acta Endocr. (Copenh.)*, 122: 569-576 (1990)); hyperparathyroidism (Miller, D. et al., *Canad. Med. Ass. J.* 145:227-228 (1991)); Paget's disease (Palmieri, G. M. A. et al., *J. of Bone and Mineral Research*, 7: 5240 (1992)); VIPoma (Koberstein, B. et al., *Gastroenterology* 28: 295-301 (1990); Christensen, C., *Acta Chir. Scand.*, 155: 541-543 (1989)); nesidioblastosis and hyperinsulinism (Laron, Z., *Israel J. Med. ScL*, 26: 1-2 (1990)); Wilson, D. C. et al., *Med. Sci.*, 158: 31-32 (1989)); gastrinoma (Bauer, F. E. et al., *Europ. J. Pharmacol.*, 183: 55 (1990)); Zollinger-Ellison syndrome (Mozell, E. et al., *Surg. Gynec. Obstet.*, 170: 476-484 (1990)); hypersecretory diarrhea related to AIDS and other conditions (Cello, J. P. et al., *Gastroenterology*, 98: A163 (1990)); elevated gastrin-releasing peptide levels (Alhindawi, R. et al., *Can. J Surg.*, 33: 139-142 (1990)); diarrhea associated with chemotherapy (Petrelli, N. et al., *Proc. Amer. Soc. Clin. Oncol.*, 10: 138 (1991)); irritable bowel syndrome (O'Donnell, L. J. D. et al., *Aliment. Pharmacol. Therap.*, 4: 177-181 (1990)); pancreatitis (Tulassay, Z. et al., *Gastroenterology*, 98:A238 (1990)); Crohn's disease (Fedorak, R. N. et al., *Can. J. Gastroenterology*, 3:53-57, 1989)); systemic sclerosis (Soudah, H. et al., *Gastroenterology*, 98:A129 (1990)); thyroid cancer (Modigliani, E. et al., *Ann. Endocr.*, 50: 483-488 (1989); psoriasis (Camisa, C. et al., *Cleveland Clinic J. Med.*, 57:71-76 (1990)); hypotension (Hoeldtke, R. D. et al., *Arch. Phys. Med. Rehabil*, 69: 895-898 (1988); Kooner, J. S. et al., *Brit. J. Clin. Pharmacol.* 28: 735-736 (1989)); panic attacks (Abelson, J. L. et al., *Clin. Psychopharmacol.* 10: 128-132 (1990)); sclerodoma (Soudah, H. et al., *Clin. Res., Vol.* 39, p. 303A (1991)); small bowel obstruction (Nott, D. M. et al., *Brit. J. Surg.*, 77:A691 (1990)); gastroesophageal reflux (Branch, M. S. et al., *Gastroenterology*, 100: A425 (1991)); duodenogastric reflux (Hasler, W. et al., *Gastroenterology*, 100: A448(1991)); Graves' disease (Chang, T. C. et al., *Brit. Med. J.*, 304: 158 (1992); polycystic ovary disease (Prelevic, G. M. et al., *Metabolism Clinical and Experimental*, 41: 76-79 (1992); upper gastrointestinal bleeding (Jenkins, S. A. et al., *Gut.* 33:404-407 (1992)); Arrigoni, A. et al., *American Journal of Gastroenterology*, 87: 1311 (1992)); pancreatic pseudocysts and ascites (Hartley, J. E. et al., *J. Roy. Soc. Med.*, 85:107-108 (1992); leukemia (Santini et al., 78:429A (1991)); meningioma (Koper, J. W. et al., *J. Clin. Endocr. Metab.*, 74:543-547 (1992)); and cancer cachexia (Bartlett, D. L. et al., *Surg. Forum.*, 42:14-16 (1991)).

Additionally, various studies have demonstrated the inhibitory effects of somatostatin and analogs thereof in patients with acromegaly; endocrine pancreatic tumors, such as insulinomas and glucagonomas; ectopic tumors, such as gastrinomas; and vasoactive intestinal peptide (VIP)-producing tumors. Schally A V, *Front Neuroendocrinol.*, 22: 248-91 (2001); Schally A. V., *Cancer Res.*, 48:6977-85 (1988).

In view of the foregoing, clearly needs remain for additional somatostatin analogs for use in the inhibition, prevention, and/or treatment of disease.

SUMMARY OF THE INVENTION

The present invention provides a novel series of somatostatin analogs according to Formula I, and pharmaceutically acceptable salts thereof:

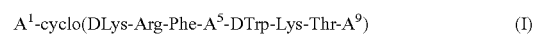

wherein:
A$^1$ is DTyr, Tyr, DLys, Lys, D2Nal, 2Nal, D1Nal, 1Nal, or absent;
A$^5$ is Phe, 2Pal, 3Pal, or 4Pal; and
A$^9$ is Phe, 2FPhe, 3FPhe, 4FPhe, 3,4FPhe, 3,5FPhe, 2,3,4,5,6FPhe, or Tyr.

Additionally, the present invention provides a novel series of somatostatin analogs according to Formula Ia, and pharmaceutically acceptable salts thereof:

wherein:
A¹ is DTyr, Tyr, DLys, Lys, D2Nal, 2Nal, D1Nal, 1Nal, or absent;
B is a pseudopeptide bond;
A⁵ is Phe, 2Pal, 3Pal, or 4Pal; and
A⁹ is Phe, 2FPhe, 3FPhe, 4FPhe, 3,4FPhe, 3,5FPhe, 2,3,4,5,6FPhe, or Tyr.

According to a preferred embodiment of the present invention, said pseudopeptide bond according to Formula Ia is psi(CH$_2$NR), as defined herein, wherein R is H, (C$_{1-10}$)alkyl, substituted (C$_{1-10}$)alkyl, (C$_{1-10}$)heteroalkyl, substituted (C$_{1-10}$)heteroalkyl, (C$_{2-10}$)alkenyl, substituted (C$_{2-10}$)alkenyl, (C$_{2-10}$)alkynyl, substituted (C$_{2-10}$)alkynyl, aryl, alkylaryl, substituted alkylaryl, arylalkyl, substituted arylalkyl, (C$_{2-10}$)acyl, or substituted (C$_{2-10}$)acyl.

Additionally, the present invention provides a novel series of compounds according to Formula II, and pharmaceutically acceptable salts thereof:

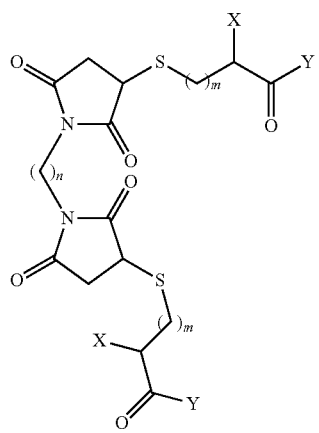

(II)

wherein:
n is 1-10;
m is 1-6;
X is H, H$_2$N, or Ac—HN; and
Y is, independent for each occurrence, a somatostatin analog according to Formula I or Formula Ia.

Additionally, the present invention provides a novel series of compounds according to Formula III, and pharmaceutically acceptable salts thereof:

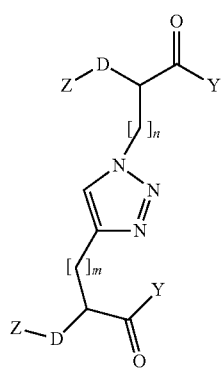

(III)

wherein:
Z is, independent for each occurrence, H or CH$_3$—(CH$_2$)$_s$—C(O)—;
D is, independent for each occurrence, NH or absent;
s is 0-17;
each of m and n is, independent for each occurrence, 0-6; and
Y is, independent for each occurrence, a somatostatin analog according to Formula I or Formula Ia.

Additionally, the present invention provides a novel series of compounds according to Formula IIIa, and pharmaceutically acceptable salts thereof:

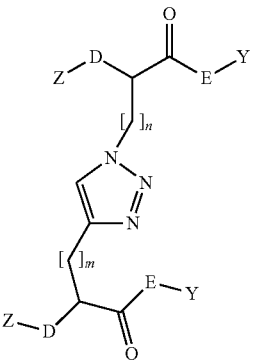

(IIIa)

wherein:
Z is, independent for each occurrence, H or CH$_3$—(CH$_2$)$_s$—C(O)—;
D is, independent for each occurrence, NH or absent;
E is, independent for each occurrence, (Aepa)$_m$, (Doc)$_n$, —[C(O)—(CH$_2$)$_p$—C(O)]$_m$—, (Aepa)$_m$, -(Doc)$_n$, (Doc)$_n$-(Aepa)$_m$, —[C(O)—(CH$_2$)$_p$—C(O)]$_m$-(Aepa)$_m$-(Doc)$_n$, —[C(O)—(CH$_2$)$_p$—C(O)]$_m$-(Doc)$_n$-(Aepa)$_m$, or absent;
s is 0-17;
each of m and n is, independent for each occurrence, 0-6;
p is 2-5; and
Y is, independent for each occurrence, a somatostatin analog according to Formula I or Formula Ia.

The present invention further provides pharmaceutical compositions comprising the somatostatin-dopamine chimeric compounds of the invention.

The present invention further provides in vitro and in vivo uses of the claimed compounds and pharmaceutical compositions.

DETAILED DESCRIPTION OF THE INVENTION

Definitions

The nomenclature used to define the peptides is that typically used in the art wherein the amino group at the N-terminus appears to the left and the carboxyl group at the C-terminus appears to the right. Where an amino acid has isomeric forms, it is the L form of the amino acid that is represented unless otherwise explicitly indicated, e.g., "DLys" for D-lysine.

Lines between amino acid residues, unless otherwise defined, represent peptide bonds between the amino acid residues. The Greek letter ψ, designated herein as "psi", is used herein to indicate that a peptide bond (i.e., amide bond) has been replaced by a pseudopeptide bond (e.g., reduced amide bond). As used herein, the format of the psi term is X-psi(CH$_2$NR)—X', wherein X is an amino acyl radical whose carbonyl group has been modified to CH$_2$, and wherein X' is an amino acyl radical whose α-amino group has been modified to NR, wherein R is, e.g., H, (C$_{1-10}$)alkyl or (C$_{2-10}$)acyl.

Some of the compounds of the instant invention have at least one asymmetric center. Additional asymmetric centers may be present in the molecule depending upon the nature of the various substituents of the molecule. Each such asymmetric center will produce two optical isomers and it is intended that all such optical isomers, as separated, pure or partially purified optical isomers, racemic mixtures or diastereomeric mixtures thereof, are included within the scope of the instant invention.

The nomenclature for the somatostatin receptor subtypes is in accordance with the recommendations of IUPHAR, in which SSTR-4 refers to the receptor originally cloned by Bruno et al., and SSTR-5 refers to the receptor cloned by O'Carroll et al.

By "alkyl", e.g., (C$_{1-10}$)alkyl, is meant a hydrocarbon group containing one or more carbon atoms, where multiple carbon atoms if present are joined by single bonds. The alkyl hydrocarbon group may be straight-chain or contain one or more branches or cyclic groups.

By "substituted alkyl", e.g., substituted (C$_{1-10}$)alkyl, is meant an alkyl wherein one or more hydrogen atoms of the hydrocarbon group are replaced with one or more substituents selected from the group consisting of halogen (i.e., fluorine, chlorine, bromine, and iodine), —OH, —CN, —SH, —NH$_2$, —NHCH$_3$, —NO$_2$, —(C$_{1-2}$)alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present. The presence of —(CH$_2$)$_{0-4}$—COOH results in the production of an alkyl acid. Examples of alkyl acids containing, or consisting of, —(CH$_2$)$_{0-4}$—COOH include 2-norbornane acetic acid, tert-butyric acid and 3-cyclopentyl propionic acid.

By "heteroalkyl", e.g., (C$_{1-10}$)heteroalkyl, is meant an alkyl wherein one of more of the carbon atoms in the hydrocarbon group are replaced with one or more of the following groups: amino, amido, —O—, or carbonyl. In different embodiments 1 or 2 heteroatoms are present.

By "substituted heteroalkyl", e.g., substituted (C$_{1-10}$)heteroalkyl, is meant a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —(C$_{1-2}$) alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "alkenyl", e.g., (C$_{2-10}$)alkenyl, is meant a hydrocarbon group made up of two or more carbons where one or more carbon-carbon double bonds are present. The alkenyl hydrocarbon group may be straight-chain or contain one or more branches or cyclic groups.

By "substituted alkenyl", e.g., substituted (C$_{2-10}$)alkenyl, is meant an alkenyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —(C$_{1-2}$)alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "alkynyl", e.g., (C$_{2-10}$)alkynyl, is meant a hydrocarbon group made up of two or more carbons where one or more carbon-carbon triple bonds are present. The alkynyl hydrocarbon group may be straight-chain or contain one or more branches or cyclic groups.

By "substituted alkynyl", e.g., substituted (C$_{2-10}$)alkynyl, is meant an alkynyl wherein one or more hydrogen atoms of the hydrocarbon group are replaced with one or more substituents selected from the group consisting of a halogen (i.e., fluorine, chlorine, bromine, and iodine), —OH, —CN, —SH, —NH$_2$, —NHCH$_3$, —NO$_2$, —(C$_{1-2}$)alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "aryl" is meant an optionally substituted aromatic group with at least one ring having a conjugated pi-electron system, containing up to two conjugated or fused ring systems. An aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, and quinoline, 2-imidazole, and 9-anthracene. Aryl substituents are selected from the group consisting of —C$_{1-4}$ alkyl, —C$_{1-4}$ alkoxy, halogen (i.e., fluorine, chlorine, bromine, and iodine), —OH, —CN, —SH, —NH$_2$, —NO$_2$, —(C$_{1-2}$)alkyl substituted with 1 to 5 halogens, —CF$_3$, —OCF$_3$, and —(CH$_2$)$_{0-4}$—COOH. In different embodiments the aryl contains 0, 1, 2, 3, or 4 substituents.

By "acyl", e.g., (C$_{2-10}$)acyl, is meant X'—R"—C(O)—, where R" is alkyl, substituted alkyl, heteroalkyl, substituted heteroalkyl, alkenyl, substituted alkenyl, alkynyl, substituted alkynyl, aryl, alkylaryl, or substituted alklyaryl and X' is H or absent.

By "arylalkyl" or "alkylaryl" is meant an "alkyl" joined to an "aryl".

By a "somatostatin receptor agonist" is meant a compound that has a high binding affinity (e.g., K$_i$ of less than 100 nM, or preferably less than 10 nM, or more preferably less than 1 nM) for a somatostatin receptor (e.g., as defined by the receptor binding assay described below), such as any of the different subtypes: e.g., SSTR1, SSTR2, SSTR3, SSTR4, and SSTR5, and elicits a somatostatin-like effect; for example, in an assay for the inhibition of cAMP intracellular production.

By a "somatostatin selective agonist" is meant a somatostatin receptor agonist which has a higher binding affinity (e.g., lower K$_i$) and/or potency (e.g., low EC$_{50}$) for one somatostatin receptor subtype than for any other somatostatin receptor subtype, such as, for example, a somatostatin SSTR2 selective agonist.

Hydrogen atoms are not always shown in organic structural diagrams (e.g., at the end of a drawn line representing a CH$_3$ group) or may be only selectively shown in some structural diagrams, as the presence and location of hydrogen atoms in organic molecular structures are understood and known by persons skilled in the art. Likewise, carbon atoms are not always specifically abbreviated with "C", as the presence and location of carbon atoms in structural diagrams are known and understood by persons skilled in the art.

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristics of the composition or method. It is also understood that any composition or method described herein as "comprising" or "consisting essentially of" one or more named elements or steps also describes the corresponding, more limited, and closed-ended composition or method "consisting of" (or which "consists of") the named elements or steps to the exclusion of any other unnamed element or step. In any composition or method disclosed herein, known or disclosed equivalents of any named essential element or step may be substituted for that element or step. It is also understood that an element or step "selected from the group consisting of" refers to one or more of the elements or steps in the list that follows, including combinations of any two or more of the listed elements or steps.

In the context of therapeutic use of the somatostatin analogs compounds described herein, the terms "treatment", "to treat", or "treating" will refer to any use of the compounds calculated or intended to correct or reduce the disease conditions of patients, e.g., to arrest or inhibit the growth or proliferation of neuroendocrine tumors and/or alleviation of a symptom of neuroendocrine disease and other conditions. Thus, treating an individual may be carried out after any diagnosis indicating possible presence of neuroendocrine tumor or neuro endocrine disease.

The meaning of other terms will be understood by the context as understood by the skilled practitioner in the art, including the fields of organic chemistry, pharmacology, and physiology.

Abbreviations

Abbreviations of the common amino acids are in accordance with the recommendations of IUPAC-IUB. In Formulas I and Ia, and in the chemical names as listed in Table I, the following abbreviations for amino acids are used: "Lys" for lysine; "Arg" for arginine; "Phe" for phenylalanine; "Trp" for tryptophan; "Thr" for threonine; "2Pal" for β-(2-pyridinyl)alanine; "3Pal" for β-(3-pyridinyl)alanine; "4Pal" for β-(4-pyridinyl)alanine; "Tyr" for tyrosine; "1Nal" for β-(1-naphthyl)alanine; "2Nal" for β-(2-naphthyl)alanine; and "2FPhe, 3FPhe, 4FPhe, 3,4FPhe, 3,5FPhe, or 2,3,4,5,6FPhe" for phenylalanine fluorinated at each of the designated positions of the phenyl ring.

Certain abbreviations used herein are defined as follows:
By "Ac" is meant acetyl.
By "Aepa" is meant 4-(2-aminoethyl)-1-carboxy methylpiperazine, represented by the structure:

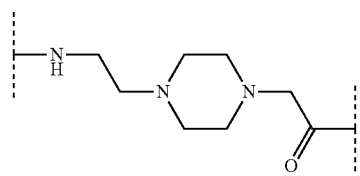

By "Boc" is meant tert-butyloxycarbonyl.
By "BSA" is meant bovine serum albumin.
By "DCM" is meant dichloromethane.
By "DIEA" is meant diisopropylethyl amine.
By "DMF" is meant dimethylformamide.
By "Doc" is meant 8-amino-3,6-dioxaoctanoic acid, represented by the structure:

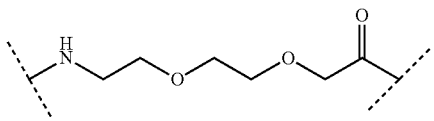

By "DTT" is meant dithiothreitol.
By "EDTA" is meant ethylenediaminetetraacetic acid.
By "EGTA" is meant ethylene glycol tetraacetic acid.
By "ESI-MS" is meant electrospray ionization mass spectrometry.
By "Fmoc" is meant fluorenylmethyloxycarbonyl.
By "HCTU" is meant (2-(6-chloro-1H-benzotriazole-1-yl)-1,1,3,3-tetramethylaminium hexafluorophosphate)
By "HOBt" is meant 1-hydroxy-benzotriazole.
By "Mtt" is meant 4-methyltrityl.
By "Pbf" is meant 2,2,4,6,7-pentamethyldihydrobenzofuran-5-sulfonyl.
By "PyAOP" is meant (7-azabenzotriazol-1-yloxy)tripyrrolidinophosphonium hexafluorophosphate).
By "tBu" is meant tert-butyl.
By "TIS" is meant triisopropylsilane.
By "Trt" is meant trityl.
By "TFA" is meant trifluoroacetic acid.

EMBODIMENTS OF THE INVENTION

In the compounds of Formulas I, Ia, II, III, and Ma, $A^1$ is DTyr, Tyr, DLys, Lys, D2Nal, 2Nal, D1Nal, 1Nal, or absent. In some embodiments, $A^1$ is DTyr, Tyr, DLys, Lys, or absent. In some embodiments, $A^1$ is Tyr, Lys, or absent. In some embodiments, $A^1$ is Tyr or Lys. In some embodiments, $A^1$ is Tyr or absent. In some embodiments, $A^1$ is Lys or absent. In certain particular embodiments, $A^1$ is absent. In certain other particular embodiments, $A^1$ is Tyr.

In the compounds of Formulas I I, Ia, II, III, and IIIa, $A^5$ is Phe, 2Pal, 3Pal, or 4Pal. In some embodiments, $A^5$ is Phe or 4Pal. In certain particular embodiments $A^5$ is 4Pal.

In the compounds of Formulas I, Ia, II, III, and Ma, $A^9$ is Phe, 2FPhe, 3FPhe, 4FPhe, 3,4FPhe, 3,5FPhe, 2,3,4,5,6FPhe, or Tyr. In some embodiments, $A^9$ is Phe, 4FPhe, or Tyr. In certain particular embodiments, $A^9$ is Tyr.

In the compounds of Formulas I, Ia, II, III, and Ma, in some embodiments, $A^1$ is acylated with RC(O), wherein R is $C_{1-10}$ alkyl. In some embodiments, $A^1$ is acetylated.

Select compounds according to the present invention are provided in Table I.

TABLE I
| Compound No. | Chemical Name; Corresponding Structural Representations |
|---|---|
| 1 | cyclo(DLys-Arg-Phe-4Pal-DTrp-Lys-Thr-Phe); |
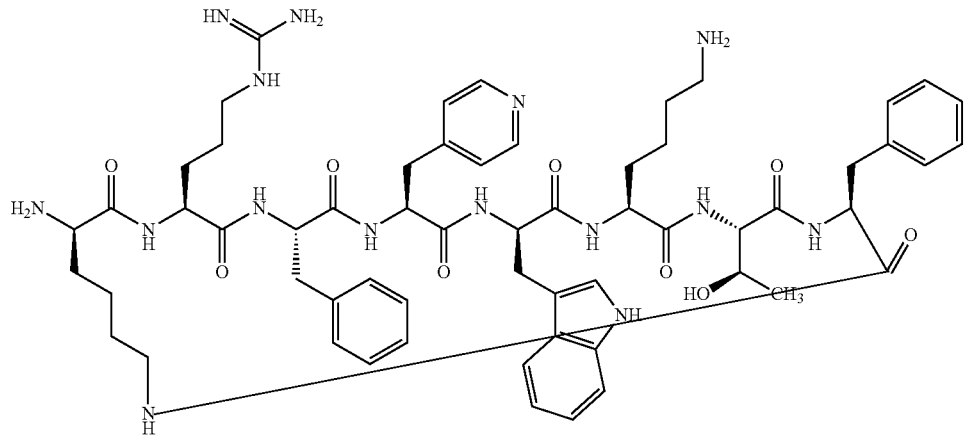 [SMILES: C[C@@H](O)[C@H](NC(=O)[C@H](CCCCN)NC(=O)[C@@H](Cc1c[nH]c2ccccc12)NC(=O)[C@H](Cc1ccncc1)NC(=O)[C@H](Cc1ccccc1)NC(=O)[C@H](CCCNC(=N)N)NC(=O)[C@H](N)CCCCN)C(=O)N[C@H](CC=O)Cc1ccccc1]
2 cyclo(DLys-Arg-Phe-Phe-DTrp-Lys-Thr-Phe);
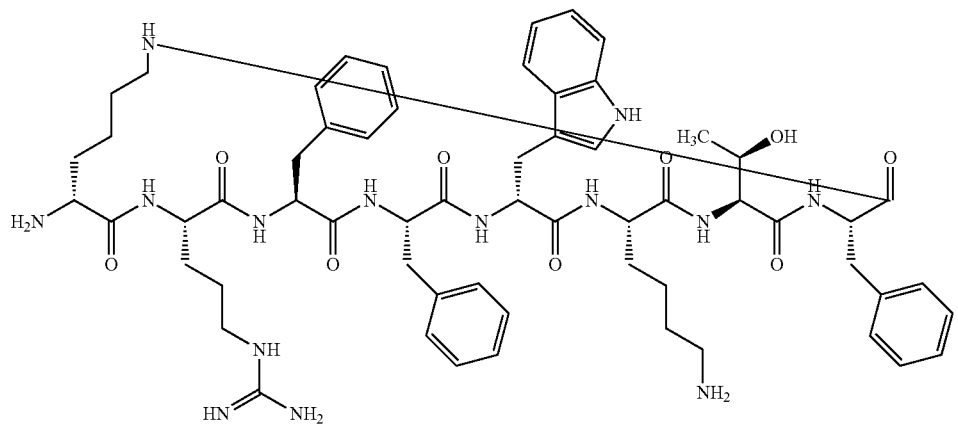 [SMILES: C[C@@H](O)[C@H](NC(=O)[C@H](CCCCN)NC(=O)[C@@H](Cc1c[nH]c2ccccc12)NC(=O)[C@H](Cc1ccccc1)NC(=O)[C@H](Cc1ccccc1)NC(=O)[C@H](CCCNC(=N)N)NC(=O)[C@H](N)CCCCN)C(=O)N[C@H](C=O)Cc1ccccc1]
3 cyclo(DLys-Arg-Phe-4Pal-DTrp-Lys-Thr-Tyr);
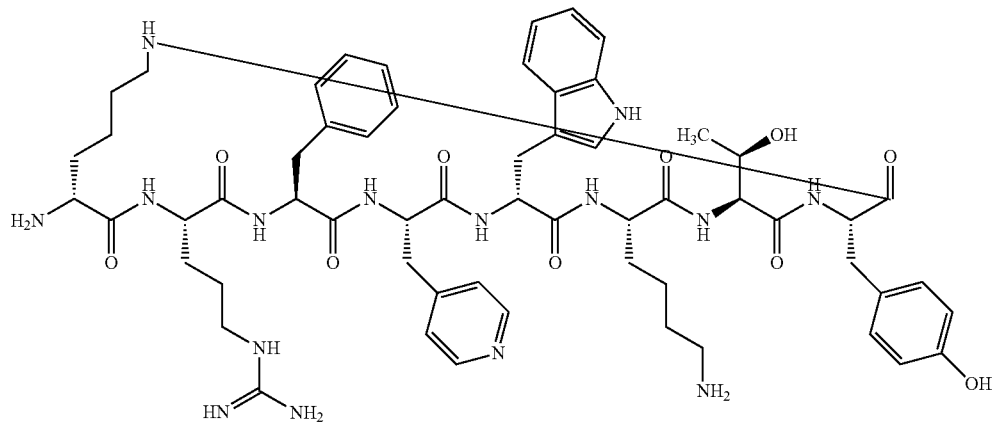 [SMILES: C[C@@H](O)[C@H](NC(=O)[C@H](CCCCN)NC(=O)[C@@H](Cc1c[nH]c2ccccc12)NC(=O)[C@H](Cc1ccncc1)NC(=O)[C@H](Cc1ccccc1)NC(=O)[C@H](CCCNC(=N)N)NC(=O)[C@H](N)CCCCN)C(=O)N[C@H](C=O)Cc1ccc(O)cc1]

| Compound No. | Chemical Name; Corresponding Structural Representations |
|---|---|
| 4 | cyclo(DLys-Arg-Phe-Phe-DTrp-Lys-Thr-4FPhe); |
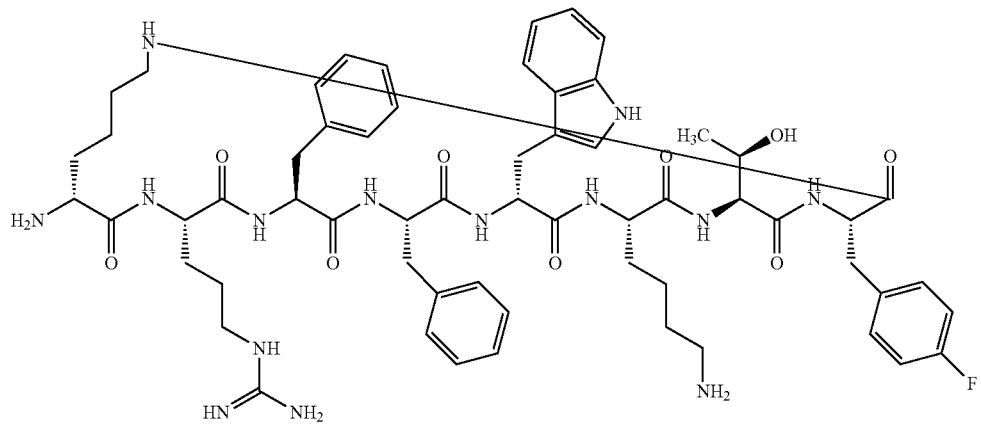 [SMILES: C[C@@H](O)[C@H](NC(=O)[C@H](CCCCN)NC(=O)[C@@H](Cc1c[nH]c2ccccc12)NC(=O)[C@H](Cc1ccccc1)NC(=O)[C@H](Cc1ccccc1)NC(=O)[C@H](CCCNC(=N)N)NC(=O)[C@H](N)CCCCN)C(=O)N[C@H](C=O)Cc1ccc(F)cc1]
| | |
|---|---|
| 5 | 1-[(ethan-2-oyl)-Tyr-psi(CH$_2$NH)-cyclo(DLys-Arg-Phe-4Pal-DTrp-Lys-Thr-Phe)],4-[(propan-3-oyl)-Tyr-psi(CH$_2$NH)-cyclo(DLys-Arg-Phe-4Pal-DTrp-Lys-Thr-Phe)]-1,2,3-triazole; |
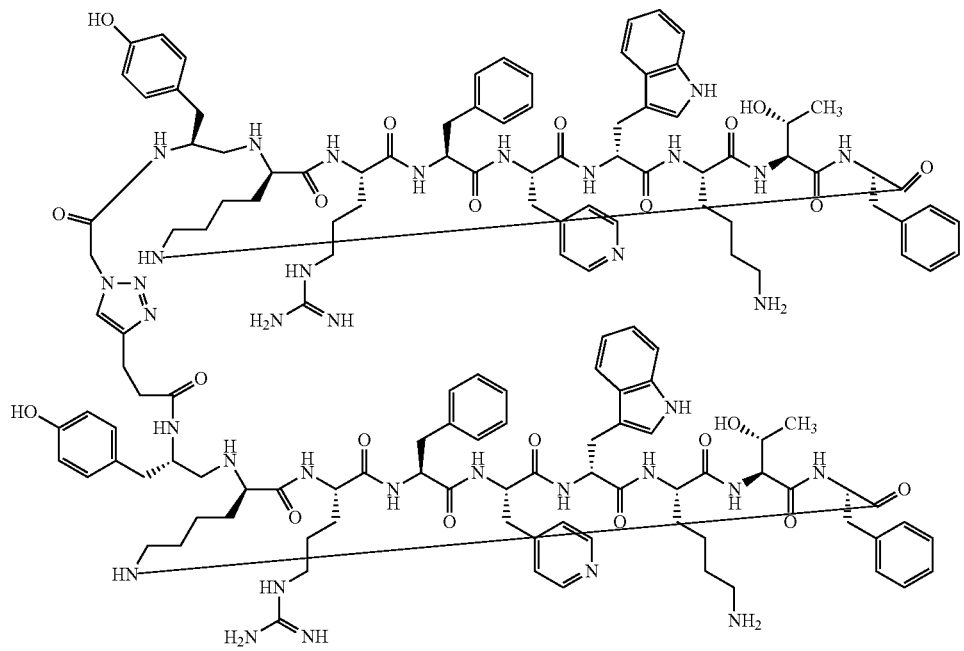 [SMILES: C[C@@H](O)[C@H](NC(=O)[C@H](CCCCN)NC(=O)[C@@H](Cc1c[nH]c2ccccc12)NC(=O)[C@H](Cc1ccncc1)NC(=O)[C@H](Cc1ccccc1)NC(=O)[C@H](CCCNC(=N)N)NC(=O)[C@@H](CCCCN)NC[C@H](Cc1ccc(O)cc1)NCCC(=O)Cn1cc(CCC(=O)N[C@H](CN[C@H](CCCCN)C(=O)N[C@@H](CCCNC(=N)N)C(=O)N[C@@H](Cc2ccccc2)C(=O)N[C@@H](Cc2ccncc2)C(=O)N[C@H](Cc2c[nH]c3ccccc23)C(=O)N[C@@H](CCCCN)C(=O)N[C@H](C(=O)N[C@@H](C=O)Cc2ccccc2)[C@@H](C)O)Cc2ccc(O)cc2)nn1)C(=O)N[C@@H](C=O)Cc1ccccc1]

TABLE I-continued

| Com- pound No. | Chemical Name; Corresponding Structural Representations |
|---|---|
| 6 | 1-[(ethan-2-oyl)-Tyr-psi(CH₂NH)-cyclo(DLys-Arg-Phe-Phe-DTrp-Lys-Thr-4FPhe)],4-[(propan-3-oyl)-Tyr-psi(CH₂NH)-cyclo(DLys-Arg-Phe-Phe-DTrp-Lys-Thr-4FPhe)]-1,2,3-triazole; |

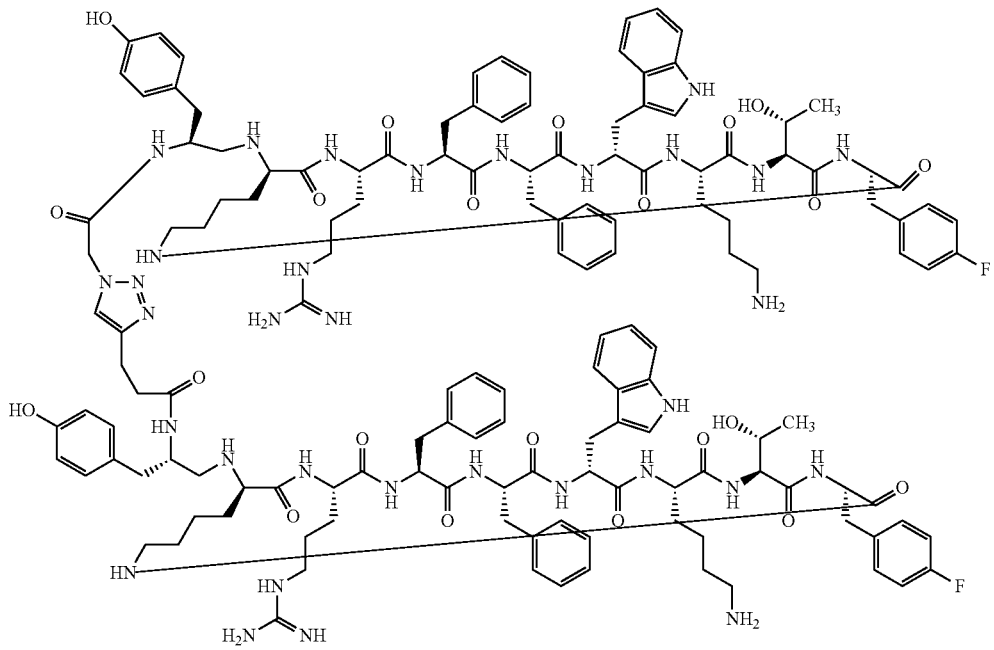 [SMILES: C[C@@H](O)[C@H](NC(=O)[C@H](CCCCN)NC(=O)[C@@H](Cc1c[nH]c2ccccc12)NC(=O)[C@H](Cc1ccccc1)NC(=O)[C@H](Cc1ccccc1)NC(=O)[C@H](CCCNC(=N)N)NC(=O)[C@@H](CCCCN)NC[C@H](Cc1ccc(O)cc1)NCCC(=O)Cn1cc(CCC(=O)N[C@H](CN[C@H](CCCCN)C(=O)N[C@@H](CCCNC(=N)N)C(=O)N[C@@H](Cc2ccccc2)C(=O)N[C@@H](Cc2ccccc2)C(=O)N[C@H](Cc2c[nH]c3ccccc23)C(=O)N[C@@H](CCCCN)C(=O)N[C@H](C(=O)N[C@@H](C=O)Cc2ccc(F)cc2)[C@@H](C)O)Cc2ccc(O)cc2)nn1)C(=O)N[C@@H](C=O)Cc1ccc(F)cc1]

| | |
|---|---|
| 7 | 1-[(ethan-2-oyl)-Tyr-psi(CH₂NH)-cyclo(DLys-Arg-Phe-Phe-DTrp-Lys-Thr-Tyr)],4-[(propan-3-oyl)-Tyr-psi(CH₂NH)-cyclo(DLys-Arg-Phe-Phe-DTrp-Lys-Thr-Tyr)]-1,2,3-triazole; |

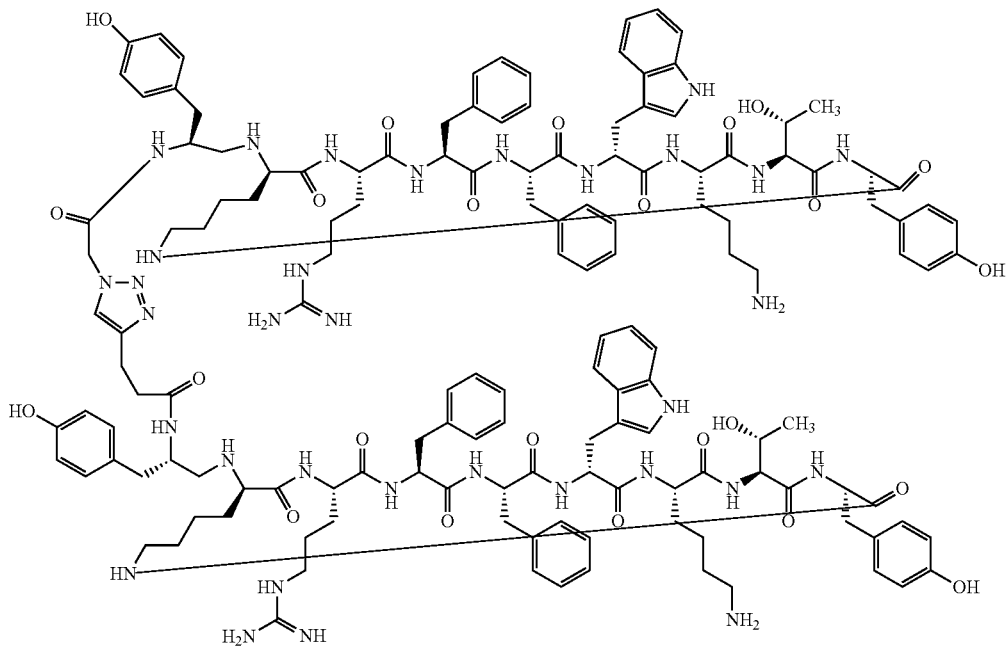 [SMILES: C[C@@H](O)[C@H](NC(=O)[C@H](CCCCN)NC(=O)[C@@H](Cc1c[nH]c2ccccc12)NC(=O)[C@H](Cc1ccccc1)NC(=O)[C@H](Cc1ccccc1)NC(=O)[C@H](CCCNC(=N)N)NC(=O)[C@@H](CCCCN)NC[C@H](Cc1ccc(O)cc1)NCCC(=O)Cn1cc(CCC(=O)N[C@H](CN[C@H](CCCCN)C(=O)N[C@@H](CCCNC(=N)N)C(=O)N[C@@H](Cc2ccccc2)C(=O)N[C@@H](Cc2ccccc2)C(=O)N[C@H](Cc2c[nH]c3ccccc23)C(=O)N[C@@H](CCCCN)C(=O)N[C@H](C(=O)N[C@@H](C=O)Cc2ccc(O)cc2)[C@@H](C)O)Cc2ccc(O)cc2)nn1)C(=O)N[C@@H](C=O)Cc1ccc(O)cc1]

| | |
|---|---|
| 8 | 1-[(ethan-2-oyl)-Tyr-psi(CH₂NH)-cyclo(DLys-Arg-Phe-Phe-DTrp-Lys-Thr-Phe)],4-[(propan-3-oyl)-Tyr-psi(CH₂NH)-cyclo(DLys-Arg-Phe-Phe-DTrp-Lys-Thr-Phe)]-1,2,3-triazole |
| 9 | 1-[(ethan-2-oyl)-Tyr-psi(CH₂NH)-cyclo(DLys-Arg-Phe-4Pal-DTrp-Lys-Thr-Tyr)],4-[(propan-3-oyl)-Tyr-psi(CH₂NH)-cyclo(DLys-Arg-Phe-4Pal-DTrp-Lys-Thr-Tyr)]-1,2,3-triazole |
| 10 | DTyr-cyclo(DLys-Arg-Phe-Phe-DTrp-Lys-Thr-Phe) |
| 11 | DTyr-cyclo(DLys-Arg-Phe-4Pal-DTrp-Lys-Thr-Tyr) |

| Com- pound No. | Chemical Name; Corresponding Structural Representations |
|---|---|
| 12 | DTyr-cyclo(DLys-Arg-Phe-Phe-DTrp-Lys-Thr-4FPhe); |

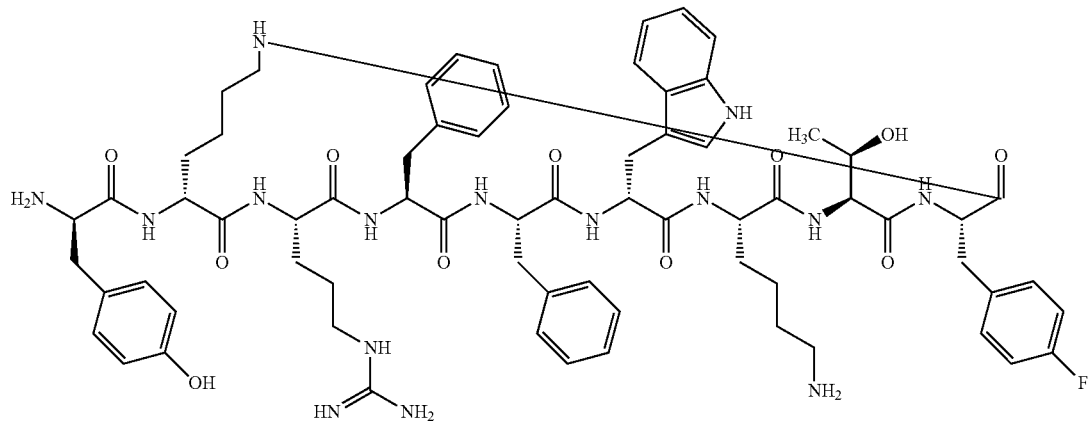 [SMILES: C[C@@H](O)[C@H](NC(=O)[C@H](CCCCN)NC(=O)[C@@H](Cc1c[nH]c2ccccc12)NC(=O)[C@H](Cc1ccccc1)NC(=O)[C@H](Cc1ccccc1)NC(=O)[C@H](CCCNC(=N)N)NC(=O)[C@@H](CCCCN)NC(=O)[C@H](N)Cc1ccc(O)cc1)C(=O)N[C@H](C=O)Cc1ccc(F)cc1]

| | |
|---|---|
| 13 | DTyr-psi(CH$_2$NH)-cyclo(DLys-Arg-Phe-4Pal-DTrp-Lys-Thr-Phe) |
| 14 | DTyr-psi(CH$_2$NH)-cyclo(DLys-Arg-Phe-Phe-DTrp-Lys-Thr-Phe) |
| 15 | DTyr-psi(CH$_2$NH)-cyclo(DLys-Arg-Phe-4Pal-DTrp-Lys-Thr-Tyr) |
| 16 | DTyr-psi(CH$_2$NH)-cyclo(DLys-Arg-Phe-Phe-DTrp-Lys-Thr-4FPhe) |
| 17 | Tyr-cyclo(DLys-Arg-Phe-4Pal-DTrp-Lys-Thr-Phe); |

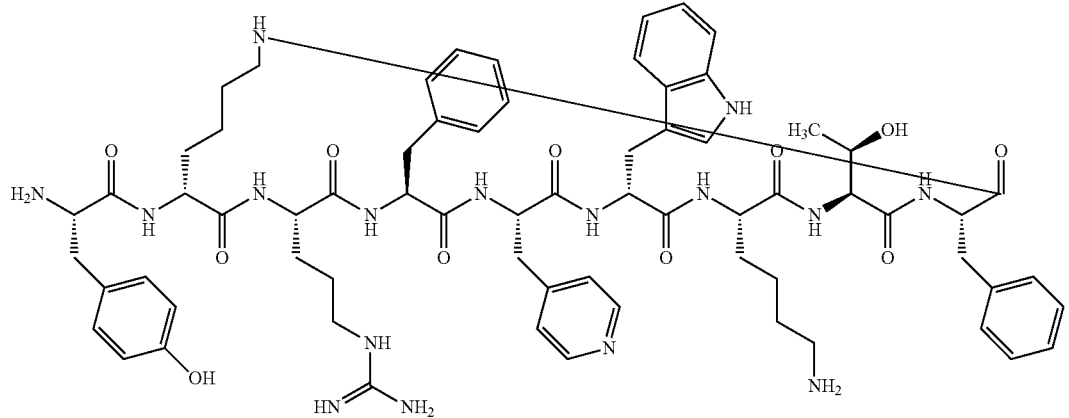 [SMILES: C[C@@H](O)[C@H](NC(=O)[C@H](CCCCN)NC(=O)[C@@H](Cc1c[nH]c2ccccc12)NC(=O)[C@H](Cc1ccncc1)NC(=O)[C@H](Cc1ccccc1)NC(=O)[C@H](CCCNC(=N)N)NC(=O)[C@@H](CCCCN)NC(=O)[C@@H](N)Cc1ccc(O)cc1)C(=O)N[C@H](C=O)Cc1ccccc1]

| | |
|---|---|
| 18 | Tyr-cyclo(DLys-Arg-Phe-Phe-DTrp-Lys-Thr-Phe) |
| 19 | Tyr-cyclo(DLys-Arg-Phe-4Pal-DTrp-Lys-Thr-Tyr); |

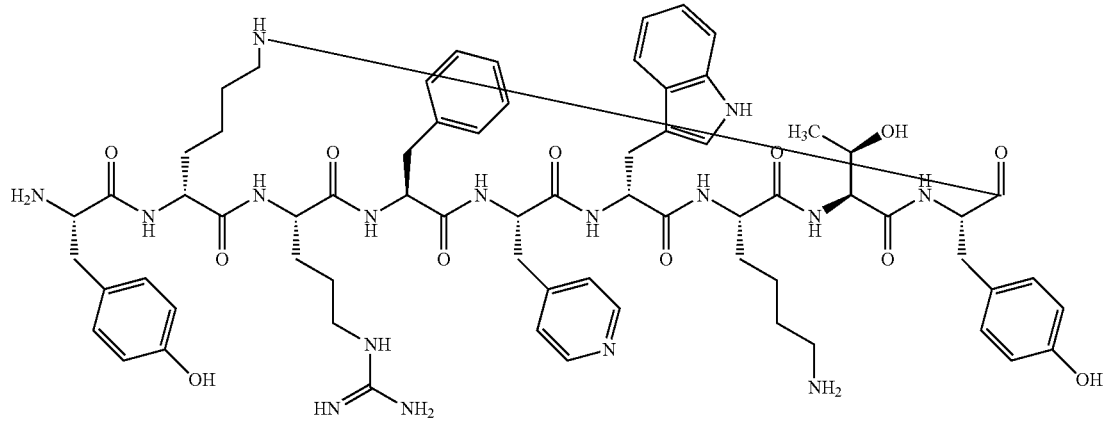 [SMILES: C[C@@H](O)[C@H](NC(=O)[C@H](CCCCN)NC(=O)[C@@H](Cc1c[nH]c2ccccc12)NC(=O)[C@H](Cc1ccncc1)NC(=O)[C@H](Cc1ccccc1)NC(=O)[C@H](CCCNC(=N)N)NC(=O)[C@@H](CCCCN)NC(=O)[C@@H](N)Cc1ccc(O)cc1)C(=O)N[C@H](C=O)Cc1ccc(O)cc1]

TABLE I-continued

| Compound No. | Chemical Name; Corresponding Structural Representations |
| --- | --- |
| 20 | Tyr-cyclo(DLys-Arg-Phe-Phe-DTrp-Lys-Thr-4FPhe) |
| 21 | Tyr-psi(CH₂NH)-cyclo(DLys-Arg-Phe-4Pal-DTrp-Lys-Thr-Phe); |
| 22 | Tyr-psi(CH₂NH)-cyclo(DLys-Arg-Phe-Phe-DTrp-Lys-Thr-Phe) |
| 23 | Tyr-psi(CH₂NH)-cyclo(DLys-Arg-Phe-4Pal-DTrp-Lys-Thr-Tyr) |
| 24 | Tyr-psi(CH₂NH)-cyclo(DLys-Arg-Phe-Phe-DTrp-Lys-Thr-4FPhe) |
| 25 | D2Nal-cyclo(DLys-Arg-Phe-4Pal-DTrp-Lys-Thr-Phe) |
| 26 | D2Nal-cyclo(DLys-Arg-Phe-Phe-DTrp-Lys-Thr-Phe) |
| 27 | D2Nal-cyclo(DLys-Arg-Phe-4Pal-DTrp-Lys-Thr-Tyr) |
| 28 | D2Nal-cyclo(DLys-Arg-Phe-Phe-DTrp-Lys-Thr-4FPhe) |
| 29 | D2Nal-psi(CH₂NH)-cyclo(DLys-Arg-Phe-4Pal-DTrp-Lys-Thr-Phe) |
| 30 | D2Nal-psi(CH₂NH)-cyclo(DLys-Arg-Phe-Phe-DTrp-Lys-Thr-Phe) |
| 31 | D2Nal-psi(CH₂NH)-cyclo(DLys-Arg-Phe-4Pal-DTrp-Lys-Thr-Tyr) |
| 32 | D2Nal-psi(CH₂NH)-cyclo(DLys-Arg-Phe-Phe-DTrp-Lys-Thr-4FPhe) |
| 33 | 2Nal-cyclo(DLys-Arg-Phe-4Pal-DTrp-Lys-Thr-Phe) |
| 34 | 2Nal-cyclo(DLys-Arg-Phe-Phe-DTrp-Lys-Thr-Phe) |
| 35 | 2Nal-cyclo(DLys-Arg-Phe-4Pal-DTrp-Lys-Thr-Tyr) |
| 36 | 2Nal-cyclo(DLys-Arg-Phe-Phe-DTrp-Lys-Thr-4FPhe) |
| 37 | 2Nal-psi(CH₂NH)-cyclo(DLys-Arg-Phe-4Pal-DTrp-Lys-Thr-Phe) |
| 38 | 2Nal-psi(CH₂NH)-cyclo(DLys-Arg-Phe-Phe-DTrp-Lys-Thr-Phe) |
| 39 | 2Nal-psi(CH₂NH)-cyclo(DLys-Arg-Phe-4Pal-DTrp-Lys-Thr-Tyr) |
| 40 | 2Nal-psi(CH₂NH)-cyclo(DLys-Arg-Phe-Phe-DTrp-Lys-Thr-4FPhe) |
| 41 | D1Nal-cyclo(DLys-Arg-Phe-4Pal-DTrp-Lys-Thr-Phe) |
| 42 | D1Nal-cyclo(DLys-Arg-Phe-Phe-DTrp-Lys-Thr-Phe) |
| 43 | D1Nal-cyclo(DLys-Arg-Phe-4Pal-DTrp-Lys-Thr-Tyr) |
| 44 | D1Nal-cyclo(DLys-Arg-Phe-Phe-DTrp-Lys-Thr-4FPhe) |
| 45 | D1Nal-psi(CH₂NH)-cyclo(DLys-Arg-Phe-4Pal-DTrp-Lys-Thr-Phe) |
| 46 | D1Nal-psi(CH₂NH)-cyclo(DLys-Arg-Phe-Phe-DTrp-Lys-Thr-Phe) |
| 47 | D1Nal-psi(CH₂NH)-cyclo(DLys-Arg-Phe-4Pal-DTrp-Lys-Thr-Tyr) |
| 48 | D1Nal-psi(CH₂NH)-cyclo(DLys-Arg-Phe-Phe-DTrp-Lys-Thr-4FPhe) |
| 49 | 1Nal-cyclo(DLys-Arg-Phe-4Pal-DTrp-Lys-Thr-Phe) |
| 50 | 1Nal-cyclo(DLys-Arg-Phe-Phe-DTrp-Lys-Thr-Phe) |
| 51 | 1Nal-cyclo(DLys-Arg-Phe-4Pal-DTrp-Lys-Thr-Tyr) |
| 52 | 1Nal-cyclo(DLys-Arg-Phe-Phe-DTrp-Lys-Thr-4FPhe) |
| 53 | 1Nal-psi(CH₂NH)-cyclo(DLys-Arg-Phe-4Pal-DTrp-Lys-Thr-Phe) |
| 54 | 1Nal-psi(CH₂NH)-cyclo(DLys-Arg-Phe-Phe-DTrp-Lys-Thr-Phe) |
| 55 | 1Nal-psi(CH₂NH)-cyclo(DLys-Arg-Phe-4Pal-DTrp-Lys-Thr-Tyr) |
| 56 | 1Nal-psi(CH₂NH)-cyclo(DLys-Arg-Phe-Phe-DTrp-Lys-Thr-4FPhe) |
| 57 | 1-[(ethan-2-oyl)-cyclo(DLys-Arg-Phe-4Pal-DTrp-Lys-Thr-Phe)],4-[(propan-3-oyl)-cyclo(DLys-Arg-Phe-4Pal-DTrp-Lys-Thr-Phe)]-1,2,3-triazole |
| 58 | 1-[(ethan-2-oyl)-cyclo(DLys-Arg-Phe-Phe-DTrp-Lys-Thr-Phe)],4-[(propan-3-oyl)-cyclo(DLys-Arg-Phe-Phe-DTrp-Lys-Thr-Phe)]-1,2,3-triazole |
| 59 | 1-[(ethan-2-oyl)-cyclo(DLys-Arg-Phe-4Pal-DTrp-Lys-Thr-Tyr)],4-[(propan-3-oyl)-cyclo(DLys-Arg-Phe-4Pal-DTrp-Lys-Thr-Tyr)]-1,2,3-triazole |
| 60 | 1-[(ethan-2-oyl)-cyclo(DLys-Arg-Phe-Phe-DTrp-Lys-Thr-4FPhe)],4-[(propan-3-oyl)-cyclo(DLys-Arg-Phe-Phe-DTrp-Lys-Thr-4FPhe)]-1,2,3-triazole |
| 61 | 1-[(ethan-2-oyl)-DTyr-cyclo(DLys-Arg-Phe-4Pal-DTrp-Lys-Thr-Phe)],4-[(propan-3-oyl)-DTyr-cyclo(DLys-Arg-Phe-4Pal-DTrp-Lys-Thr-Phe)]-1,2,3-triazole |
| 62 | 1-[(ethan-2-oyl)-DTyr-cyclo(DLys-Arg-Phe-Phe-DTrp-Lys-Thr-Phe)],4-[(propan-3-oyl)-DTyr-cyclo(DLys-Arg-Phe-Phe-DTrp-Lys-Thr-Phe)]-1,2,3-triazole |
| 63 | 1-[(ethan-2-oyl)-DTyr-cyclo(DLys-Arg-Phe-4Pal-DTrp-Lys-Thr-Tyr)],4-[(propan-3-oyl)-DTyr-cyclo(DLys-Arg-Phe-4Pal-DTrp-Lys-Thr-Tyr)]-1,2,3-triazole |
| 64 | 1-[(ethan-2-oyl)-DTyr-cyclo(DLys-Arg-Phe-Phe-DTrp-Lys-Thr-4FPhe)],4-[(propan-3-oyl)-DTyr-cyclo(DLys-Arg-Phe-Phe-DTrp-Lys-Thr-4FPhe)]-1,2,3-triazole |
| 65 | 1-[(ethan-2-oyl)-DTyr-psi(CH₂NH)-cyclo(DLys-Arg-Phe-4Pal-DTrp-Lys-Thr-Phe)],4-[(propan-3-oyl)-DTyr-psi(CH₂NH)-cyclo(DLys-Arg-Phe-4Pal-DTrp-Lys-Thr-Phe)]-1,2,3-triazole |
| 66 | 1-[(ethan-2-oyl)-DTyr-psi(CH₂NH)-cyclo(DLys-Arg-Phe-Phe-DTrp-Lys-Thr-Phe)],4-[(propan-3-oyl)-DTyr-psi(CH₂NH)-cyclo(DLys-Arg-Phe-Phe-DTrp-Lys-Thr-Phe)]-1,2,3-triazole |

TABLE I-continued

| Compound No. | Chemical Name; Corresponding Structural Representations |
|---|---|
| 67 | 1-[(ethan-2-oyl)-DTyr-psi(CH$_2$NH)-cyclo(DLys-Arg-Phe-4Pal-DTrp-Lys-Thr-Tyr)],4-[(propan-3-oyl)-DTyr-psi(CH$_2$NH)-cyclo(DLys-Arg-Phe-4Pal-DTrp-Lys-Thr-Tyr)]-1,2,3-triazole |
| 68 | 1-[(ethan-2-oyl)-DTyr-psi(CH$_2$NH)-cyclo(DLys-Arg-Phe-Phe-DTrp-Lys-Thr-4FPhe)],4-[(propan-3-oyl)-DTyr-psi(CH$_2$NH)-cyclo(DLys-Arg-Phe-Phe-DTrp-Lys-Thr-4FPhe)]-1,2,3-triazole |
| 69 | 1-[(ethan-2-oyl)-Tyr-cyclo(DLys-Arg-Phe-4Pal-DTrp-Lys-Thr-Phe)],4-[(propan-3-oyl)-Tyr-cyclo(DLys-Arg-Phe-4Pal-DTrp-Lys-Thr-Phe)]-1,2,3-triazole |
| 70 | 1-[(ethan-2-oyl)-Tyr-cyclo(DLys-Arg-Phe-Phe-DTrp-Lys-Thr-Phe)],4-[(propan-3-oyl)-Tyr-cyclo(DLys-Arg-Phe-Phe-DTrp-Lys-Thr-Phe)]-1,2,3-triazole |
| 71 | 1-[(ethan-2-oyl)-Tyr-cyclo(DLys-Arg-Phe-4Pal-DTrp-Lys-Thr-Tyr)],4-[(propan-3-oyl)-Tyr-cyclo(DLys-Arg-Phe-4Pal-DTrp-Lys-Thr-Tyr)]-1,2,3-triazole |
| 72 | 1-[(ethan-2-oyl)-Tyr-cyclo(DLys-Arg-Phe-Phe-DTrp-Lys-Thr-4FPhe)],4-[(propan-3-oyl)-Tyr-cyclo(DLys-Arg-Phe-Phe-DTrp-Lys-Thr-4FPhe)]-1,2,3-triazole |
| 73 | 1-[(ethan-2-oyl)-D2Nal-cyclo(DLys-Arg-Phe-4Pal-DTrp-Lys-Thr-Phe)],4-[(propan-3-oyl)-D2Nal-cyclo(DLys-Arg-Phe-4Pal-DTrp-Lys-Thr-Phe)]-1,2,3-triazole |
| 74 | 1-[(ethan-2-oyl)-D2Nal-cyclo(DLys-Arg-Phe-Phe-DTrp-Lys-Thr-Phe)],4-[(propan-3-oyl)-D2Nal-cyclo(DLys-Arg-Phe-Phe-DTrp-Lys-Thr-Phe)]-1,2,3-triazole |
| 75 | 1-[(ethan-2-oyl)-D2Nal-cyclo(DLys-Arg-Phe-4Pal-DTrp-Lys-Thr-Tyr)],4-[(propan-3-oyl)-D2Nal-cyclo(DLys-Arg-Phe-4Pal-DTrp-Lys-Thr-Tyr)]-1,2,3-triazole |
| 76 | 1-[(ethan-2-oyl)-D2Nal-cyclo(DLys-Arg-Phe-Phe-DTrp-Lys-Thr-4FPhe)],4-[(propan-3-oyl)-D2Nal-cyclo(DLys-Arg-Phe-Phe-DTrp-Lys-Thr-4FPhe)]-1,2,3-triazole |
| 77 | 1-[(ethan-2-oyl)-D2Nal-psi(CH$_2$NH)-cyclo(DLys-Arg-Phe-4Pal-DTrp-Lys-Thr-Phe)],4-[(propan-3-oyl)-D2Nal-psi(CH$_2$NH)-cyclo(DLys-Arg-Phe-4Pal-DTrp-Lys-Thr-Phe)]-1,2,3-triazole |
| 78 | 1-[(ethan-2-oyl)-D2Nal-psi(CH$_2$NH)-cyclo(DLys-Arg-Phe-Phe-DTrp-Lys-Thr-Phe)],4-[(propan-3-oyl)-D2Nal-psi(CH$_2$NH)-cyclo(DLys-Arg-Phe-Phe-DTrp-Lys-Thr-Phe)]-1,2,3-triazole |
| 79 | 1-[(ethan-2-oyl)-D2Nal-psi(CH$_2$NH)-cyclo(DLys-Arg-Phe-4Pal-DTrp-Lys-Thr-Tyr)],4-[(propan-3-oyl)-D2Nal-psi(CH$_2$NH)-cyclo(DLys-Arg-Phe-4Pal-DTrp-Lys-Thr-Tyr)]-1,2,3-triazole |
| 80 | 1-[(ethan-2-oyl)-D2Nal-psi(CH$_2$NH)-cyclo(DLys-Arg-Phe-Phe-DTrp-Lys-Thr-4FPhe)],4-[(propan-3-oyl)-D2Nal-psi(CH$_2$NH)-cyclo(DLys-Arg-Phe-Phe-DTrp-Lys-Thr-4FPhe)]-1,2,3-triazole |
| 81 | 1-[(ethan-2-oyl)-D1Nal-cyclo(DLys-Arg-Phe-4Pal-DTrp-Lys-Thr-Phe)],4-[(propan-3-oyl)-D1Nal-cyclo(DLys-Arg-Phe-4Pal-DTrp-Lys-Thr-Phe)]-1,2,3-triazole |
| 82 | 1-[(ethan-2-oyl)-D1Nal-cyclo(DLys-Arg-Phe-Phe-DTrp-Lys-Thr-Phe)],4-[(propan-3-oyl)-D1Nal-cyclo(DLys-Arg-Phe-Phe-DTrp-Lys-Thr-Phe)]-1,2,3-triazole |
| 83 | 1-[(ethan-2-oyl)-D1Nal-cyclo(DLys-Arg-Phe-4Pal-DTrp-Lys-Thr-Tyr)],4-[(propan-3-oyl)-D1Nal-cyclo(DLys-Arg-Phe-4Pal-DTrp-Lys-Thr-Tyr)]-1,2,3-triazole |
| 84 | 1-[(ethan-2-oyl)-D1Nal-cyclo(DLys-Arg-Phe-Phe-DTrp-Lys-Thr-4FPhe)],4-[(propan-3-oyl)-D1Nal-cyclo(DLys-Arg-Phe-Phe-DTrp-Lys-Thr-4FPhe)]-1,2,3-triazole |
| 85 | 1-[(ethan-2-oyl)-D1Nal-psi(CH$_2$NH)-cyclo(DLys-Arg-Phe-4Pal-DTrp-Lys-Thr-Phe)],4-[(propan-3-oyl)-D1Nal-psi(CH$_2$NH)-cyclo(DLys-Arg-Phe-4Pal-DTrp-Lys-Thr-Phe)]-1,2,3-triazole |
| 86 | 1-[(ethan-2-oyl)-D1Nal-psi(CH$_2$NH)-cyclo(DLys-Arg-Phe-Phe-DTrp-Lys-Thr-Phe)],4-[(propan-3-oyl)-D1Nal-psi(CH$_2$NH)-cyclo(DLys-Arg-Phe-Phe-DTrp-Lys-Thr-Phe)]-1,2,3-triazole |
| 87 | 1-[(ethan-2-oyl)-D1Nal-psi(CH$_2$NH)-cyclo(DLys-Arg-Phe-4Pal-DTrp-Lys-Thr-Tyr)],4-[(propan-3-oyl)-D1Nal-psi(CH$_2$NH)-cyclo(DLys-Arg-Phe-4Pal-DTrp-Lys-Thr-Tyr)]-1,2,3-triazole |
| 88 | 1-[(ethan-2-oyl)-D1Nal-psi(CH$_2$NH)-cyclo(DLys-Arg-Phe-Phe-DTrp-Lys-Thr-4FPhe)],4-[(propan-3-oyl)-D1Nal-psi(CH$_2$NH)-cyclo(DLys-Arg-Phe-Phe-DTrp-Lys-Thr-4FPhe)]-1,2,3-triazole |
| 89 | 1-[(ethan-2-oyl)-Aepa-cyclo(DLys-Arg-Phe-4Pal-DTrp-Lys-Thr-Phe)],4-[(propan-3-oyl)-Aepa-cyclo(DLys-Arg-Phe-4Pal-DTrp-Lys-Thr-Phe)]-1,2,3-triazole |
| 90 | 1-[(ethan-2-oyl)-Aepa-cyclo(DLys-Arg-Phe-Phe-DTrp-Lys-Thr-Phe)],4-[(propan-3-oyl)-Aepa-cyclo(DLys-Arg-Phe-Phe-DTrp-Lys-Thr-Phe)]-1,2,3-triazole |
| 91 | 1-[(ethan-2-oyl)-Aepa-cyclo(DLys-Arg-Phe-4Pal-DTrp-Lys-Thr-Tyr)],4-[(propan-3-oyl)-Aepa-cyclo(DLys-Arg-Phe-4Pal-DTrp-Lys-Thr-Tyr)]-1,2,3-triazole |
| 92 | 1-[(ethan-2-oyl)-Aepa-cyclo(DLys-Arg-Phe-Phe-DTrp-Lys-Thr-4FPhe)],4-[(propan-3-oyl)-Aepa-cyclo(DLys-Arg-Phe-Phe-DTrp-Lys-Thr-4FPhe)]-1,2,3-triazole |
| 93 | 1-[(ethan-2-oyl)-Aepa-DTyr-cyclo(DLys-Arg-Phe-4Pal-DTrp-Lys-Thr-Phe)],4-[(propan-3-oyl)-Aepa-DTyr-cyclo(DLys-Arg-Phe-4Pal-DTrp-Lys-Thr-Phe)]-1,2,3-triazole |
| 94 | 1-[(ethan-2-oyl)-Aepa-DTyr-cyclo(DLys-Arg-Phe-Phe-DTrp-Lys-Thr-Phe)],4-[(propan-3-oyl)-Aepa-DTyr-cyclo(DLys-Arg-Phe-Phe-DTrp-Lys-Thr-Phe)]-1,2,3-triazole |
| 95 | 1-[(ethan-2-oyl)-Aepa-DTyr-cyclo(DLys-Arg-Phe-4Pal-DTrp-Lys-Thr-Tyr)],4-[(propan-3-oyl)-Aepa-DTyr-cyclo(DLys-Arg-Phe-4Pal-DTrp-Lys-Thr-Tyr)]-1,2,3-triazole |
| 96 | 1-[(ethan-2-oyl)-Aepa-DTyr-cyclo(DLys-Arg-Phe-Phe-DTrp-Lys-Thr-4FPhe)],4-[(propan-3-oyl)-Aepa-DTyr-cyclo(DLys-Arg-Phe-Phe-DTrp-Lys-Thr-4FPhe)]-1,2,3-triazole |
| 97 | 1-[(ethan-2-oyl)-Aepa-DTyr-psi(CH$_2$NH)-cyclo(DLys-Arg-Phe-4Pal-DTrp-Lys-Thr-Phe)],4-[(propan-3-oyl)-Aepa-DTyr-psi(CH$_2$NH)-cyclo(DLys-Arg-Phe-4Pal-DTrp-Lys-Thr-Phe)]-1,2,3-triazole |
| 98 | 1-[(ethan-2-oyl)-Aepa-DTyr-psi(CH$_2$NH)-cyclo(DLys-Arg-Phe-Phe-DTrp-Lys-Thr-Phe)],4-[(propan-3-oyl)-Aepa-DTyr-psi(CH$_2$NH)-cyclo(DLys-Arg-Phe-Phe-DTrp-Lys-Thr-Phe)]-1,2,3-triazole |
| 99 | 1-[(ethan-2-oyl)-Aepa-DTyr-psi(CH$_2$NH)-cyclo(DLys-Arg-Phe-4Pal-DTrp-Lys-Thr-Tyr)],4-[(propan-3-oyl)-Aepa-DTyr-psi(CH$_2$NH)-cyclo(DLys-Arg-Phe-4Pal-DTrp-Lys-Thr-Tyr)]-1,2,3-triazole |
| 100 | 1-[(ethan-2-oyl)-Aepa-DTyr-psi(CH$_2$NH)-cyclo(DLys-Arg-Phe-Phe-DTrp-Lys-Thr-4FPhe)],4-[(propan-3-oyl)-Aepa-DTyr-psi(CH$_2$NH)-cyclo(DLys-Arg-Phe-Phe-DTrp-Lys-Thr-4FPhe)]-1,2,3-triazole |
| 101 | 1-[(ethan-2-oyl)-Aepa-Tyr-cyclo(DLys-Arg-Phe-4Pal-DTrp-Lys-Thr-Phe)],4-[(propan-3-oyl)-Aepa-Tyr-cyclo(DLys-Arg-Phe-4Pal-DTrp-Lys-Thr-Phe)]-1,2,3-triazole |
| 102 | 1-[(ethan-2-oyl)-Aepa-Tyr-cyclo(DLys-Arg-Phe-Phe-DTrp-Lys-Thr-Phe)],4-[(propan-3-oyl)-Aepa-Tyr-cyclo(DLys-Arg-Phe-Phe-DTrp-Lys-Thr-Phe)]-1,2,3-triazole |
| 103 | 1-[(ethan-2-oyl)-Aepa-Tyr-cyclo(DLys-Arg-Phe-4Pal-DTrp-Lys-Thr-Tyr)],4-[(propan-3-oyl)-Aepa-Tyr-cyclo(DLys-Arg-Phe-4Pal-DTrp-Lys-Thr-Tyr)]-1,2,3-triazole |
| 104 | 1-[(ethan-2-oyl)-Aepa-Tyr-cyclo(DLys-Arg-Phe-Phe-DTrp-Lys-Thr-4FPhe)],4-[(propan-3-oyl)-Aepa-Tyr-cyclo(DLys-Arg-Phe-Phe-DTrp-Lys-Thr-4FPhe)]-1,2,3-triazole |

TABLE I-continued

| Compound No. | Chemical Name; Corresponding Structural Representations |
|---|---|
| 105 | 1-[(ethan-2-oyl)-Aepa-Tyr-psi(CH₂NH)-cyclo(DLys-Arg-Phe-4Pal-DTrp-Lys-Thr-Phe)],4-[(propan-3-oyl)-Aepa-Tyr-psi(CH₂NH)-cyclo(DLys-Arg-Phe-4Pal-DTrp-Lys-Thr-Phe)]-1,2,3-triazole |
| 106 | 1-[(ethan-2-oyl)-Aepa-Tyr-psi(CH₂NH)-cyclo(DLys-Arg-Phe-Phe-DTrp-Lys-Thr-Phe)],4-[(propan-3-oyl)-Aepa-Tyr-psi(CH₂NH)-cyclo(DLys-Arg-Phe-Phe-DTrp-Lys-Thr-Phe)]-1,2,3-triazole |
| 107 | 1-[(ethan-2-oyl)-Aepa-Tyr-psi(CH₂NH)-cyclo(DLys-Arg-Phe-4Pal-DTrp-Lys-Thr-Tyr)],4-[(propan-3-oyl)-Aepa-Tyr-psi(CH₂NH)-cyclo(DLys-Arg-Phe-4Pal-DTrp-Lys-Thr-Tyr)]-1,2,3-triazole |
| 108 | 1-[(ethan-2-oyl)-Aepa-Tyr-psi(CH₂NH)-cyclo(DLys-Arg-Phe-Phe-DTrp-Lys-Thr-4FPhe)],4-[(propan-3-oyl)-Aepa-Tyr-psi(CH₂NH)-cyclo(DLys-Arg-Phe-Phe-DTrp-Lys-Thr-4FPhe)]-1,2,3-triazole |
| 109 | 1-[(ethan-2-oyl)-Aepa-D2Nal-cyclo(DLys-Arg-Phe-4Pal-DTrp-Lys-Thr-Phe)],4-[(propan-3-oyl)-Aepa-D2Nal-cyclo(DLys-Arg-Phe-4Pal-DTrp-Lys-Thr-Phe)]-1,2,3-triazole |
| 110 | 1-[(ethan-2-oyl)-Aepa-D2Nal-cyclo(DLys-Arg-Phe-Phe-DTrp-Lys-Thr-Phe)],4-[(propan-3-oyl)-Aepa-D2Nal-cyclo(DLys-Arg-Phe-Phe-DTrp-Lys-Thr-Phe)]-1,2,3-triazole |
| 111 | 1-[(ethan-2-oyl)-Aepa-D2Nal-cyclo(DLys-Arg-Phe-4Pal-DTrp-Lys-Thr-Tyr)],4-[(propan-3-oyl)-Aepa-D2Nal-cyclo(DLys-Arg-Phe-4Pal-DTrp-Lys-Thr-Tyr)]-1,2,3-triazole |
| 112 | 1-[(ethan-2-oyl)-Aepa-D2Nal-cyclo(DLys-Arg-Phe-Phe-DTrp-Lys-Thr-4FPhe)],4-[(propan-3-oyl)-Aepa-D2Nal-cyclo(DLys-Arg-Phe-Phe-DTrp-Lys-Thr-4FPhe)]-1,2,3-triazole |
| 113 | 1-[(ethan-2-oyl)-Aepa-D2Nal-psi(CH₂NH)-cyclo(DLys-Arg-Phe-4Pal-DTrp-Lys-Thr-Phe)],4-[(propan-3-oyl)-Aepa-D2Nal-psi(CH₂NH)-cyclo(DLys-Arg-Phe-4Pal-DTrp-Lys-Thr-Phe)]-1,2,3-triazole |
| 114 | 1-[(ethan-2-oyl)-Aepa-D2Nal-psi(CH₂NH)-cyclo(DLys-Arg-Phe-Phe-DTrp-Lys-Thr-Phe)],4-[(propan-3-oyl)-Aepa-D2Nal-psi(CH₂NH)-cyclo(DLys-Arg-Phe-Phe-DTrp-Lys-Thr-Phe)]-1,2,3-triazole |
| 115 | 1-[(ethan-2-oyl)-Aepa-D2Nal-psi(CH₂NH)-cyclo(DLys-Arg-Phe-4Pal-DTrp-Lys-Thr-Tyr)],4-[(propan-3-oyl)-Aepa-D2Nal-psi(CH₂NH)-cyclo(DLys-Arg-Phe-4Pal-DTrp-Lys-Thr-Tyr)]-1,2,3-triazole |
| 116 | 1-[(ethan-2-oyl)-Aepa-D2Nal-psi(CH₂NH)-cyclo(DLys-Arg-Phe-Phe-DTrp-Lys-Thr-4FPhe)],4-[(propan-3-oyl)-Aepa-D2Nal-psi(CH₂NH)-cyclo(DLys-Arg-Phe-Phe-DTrp-Lys-Thr-4FPhe)]-1,2,3-triazole |
| 117 | 1-[(ethan-2-oyl)-Aepa-D1Nal-cyclo(DLys-Arg-Phe-4Pal-DTrp-Lys-Thr-Phe)],4-[(propan-3-oyl)-Aepa-D1Nal-cyclo(DLys-Arg-Phe-4Pal-DTrp-Lys-Thr-Phe)]-1,2,3-triazole |
| 118 | 1-[(ethan-2-oyl)-Aepa-D1Nal-cyclo(DLys-Arg-Phe-Phe-DTrp-Lys-Thr-Phe)],4-[(propan-3-oyl)-Aepa-D1Nal-cyclo(DLys-Arg-Phe-Phe-DTrp-Lys-Thr-Phe)]-1,2,3-triazole |
| 119 | 1-[(ethan-2-oyl)-Aepa-D1Nal-cyclo(DLys-Arg-Phe-4Pal-DTrp-Lys-Thr-Tyr)],4-[(propan-3-oyl)-Aepa-D1Nal-cyclo(DLys-Arg-Phe-4Pal-DTrp-Lys-Thr-Tyr)]-1,2,3-triazole |
| 120 | 1-[(ethan-2-oyl)-Aepa-D1Nal-cyclo(DLys-Arg-Phe-Phe-DTrp-Lys-Thr-4FPhe)],4-[(propan-3-oyl)-Aepa-D1Nal-cyclo(DLys-Arg-Phe-Phe-DTrp-Lys-Thr-4FPhe)]-1,2,3-triazole |
| 121 | 1-[(ethan-2-oyl)-Aepa-D1Nal-psi(CH₂NH)-cyclo(DLys-Arg-Phe-4Pal-DTrp-Lys-Thr-Phe)],4-[(propan-3-oyl)-Aepa-D1Nal-psi(CH₂NH)-cyclo(DLys-Arg-Phe-4Pal-DTrp-Lys-Thr-Phe)]-1,2,3-triazole |
| 122 | 1-[(ethan-2-oyl)-Aepa-D1Nal-psi(CH₂NH)-cyclo(DLys-Arg-Phe-Phe-DTrp-Lys-Thr-Phe)],4-[(propan-3-oyl)-Aepa-D1Nal-psi(CH₂NH)-cyclo(DLys-Arg-Phe-Phe-DTrp-Lys-Thr-Phe)]-1,2,3-triazole |
| 123 | 1-[(ethan-2-oyl)-Aepa-D1Nal-psi(CH₂NH)-cyclo(DLys-Arg-Phe-4Pal-DTrp-Lys-Thr-Tyr)],4-[(propan-3-oyl)-Aepa-D1Nal-psi(CH₂NH)-cyclo(DLys-Arg-Phe-4Pal-DTrp-Lys-Thr-Tyr)]-1,2,3-triazole |
| 124 | 1-[(ethan-2-oyl)-Aepa-D1Nal-psi(CH₂NH)-cyclo(DLys-Arg-Phe-Phe-DTrp-Lys-Thr-4FPhe)],4-[(propan-3-oyl)-Aepa-D1Nal-psi(CH₂NH)-cyclo(DLys-Arg-Phe-Phe-DTrp-Lys-Thr-4FPhe)]-1,2,3-triazole |
| 125 | DTyr-cyclo(DLys-Arg-Phe-4Pal-DTrp-Lys-Thr-Phe) |
| 126 | 1-[(ethan-2-oyl)-Doc-Doc-Tyr-psi(CH₂NH)-cyclo(DLys-Arg-Phe-Phe-DTrp-Lys-Thr-Tyr)],4-[(propan-3-oyl)-Doc-Doc-Tyr-psi(CH₂NH)-cyclo(DLys-Arg-Phe-Phe-DTrp-Lys-Thr-Tyr)]-1,2,3-triazole; |

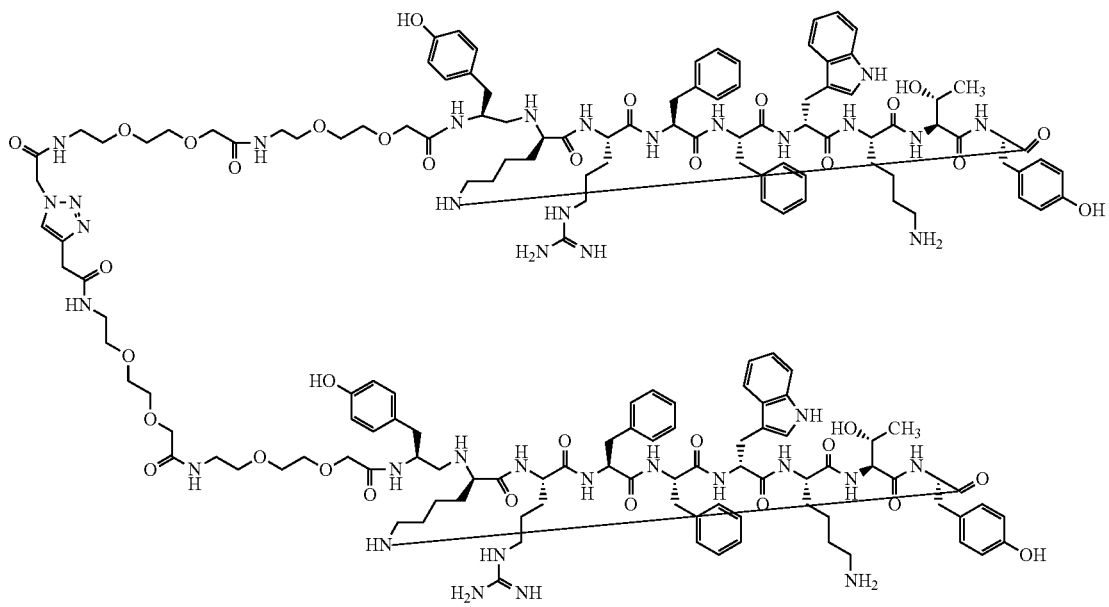 [SMILES: C[C@@H](O)[C@H](NC(=O)[C@H](CCCCN)NC(=O)[C@@H](Cc1c[nH]c2ccccc12)NC(=O)[C@H](Cc1ccccc1)NC(=O)[C@H](Cc1ccccc1)NC(=O)[C@H](CCCNC(=N)N)NC(=O)[C@@H](CCCCN)NC[C@H](Cc1ccc(O)cc1)NC(=O)COCCOCCNC(=O)COCCOCCNC(=O)Cc1cn(CC(=O)NCCOCCOCC(=O)NCCOCCOCC(=O)N[C@H](CN[C@H](CCCCN)C(=O)N[C@@H](CCCNC(=N)N)C(=O)N[C@@H](Cc2ccccc2)C(=O)N[C@@H](Cc2ccccc2)C(=O)N[C@H](Cc2c[nH]c3ccccc23)C(=O)N[C@@H](CCCCN)C(=O)N[C@H](C(=O)N[C@@H](C=O)Cc2ccc(O)cc2)[C@@H](C)O)Cc2ccc(O)cc2)nn1)C(=O)N[C@@H](C=O)Cc1ccc(O)cc1]

| 127 | Tyr-psi(CH₂NH)-cyclo(DLys-Arg-Phe-Phe-DTrp-Lys-Thr-Tyr) |

The compound according to another embodiment of the present invention comprises any of the compounds listed in Table I.

The compound according to a preferred embodiment of the present invention comprises a compound selected from the following list:

Compound 1: cyclo(DLys-Arg-Phe-4Pal-DTrp-Lys-Thr-Phe);

Compound 2: cyclo(DLys-Arg-Phe-Phe-DTrp-Lys-Thr-Phe);

Compound 3: cyclo(DLys-Arg-Phe-4Pal-DTrp-Lys-Thr-Tyr);

Compound 4: cyclo(DLys-Arg-Phe-Phe-DTrp-Lys-Thr-4FPhe);

Compound 5: 1-[(ethan-2-oyl)-Tyr-psi(CH$_2$NH)-cyclo(DLys-Arg-Phe-4Pal-DTrp-Lys-Thr-Phe)],4-[(propan-3-oyl)-Tyr-psi(CH$_2$NH)-cyclo(DLys-Arg-Phe-4Pal-DTrp-Lys-Thr-Phe)]-1,2,3-triazole;

Compound 6: 1-[(ethan-2-oyl)-Tyr-psi(CH$_2$NH)-cyclo(DLys-Arg-Phe-Phe-DTrp-Lys-Thr-4FPhe)],4-[(propan-3-oyl)-Tyr-psi(CH$_2$NH)-cyclo(DLys-Arg-Phe-Phe-DTrp-Lys-Thr-4FPhe)]-1,2,3-triazole;

Compound 7: 1-[(ethan-2-oyl)-Tyr-psi(CH$_2$NH)-cyclo(DLys-Arg-Phe-Phe-DTrp-Lys-Thr-Tyr)],4-[(propan-3-oyl)-Tyr-psi(CH$_2$NH)-cyclo(DLys-Arg-Phe-Phe-DTrp-Lys-Thr-Tyr)]-1,2,3-triazole;

Compound 125: DTyr-cyclo(DLys-Arg-Phe-4Pal-DTrp-Lys-Thr-Phe);

Compound 10: DTyr-cyclo(DLys-Arg-Phe-Phe-DTrp-Lys-Thr-Phe);

Compound 11: DTyr-cyclo(DLys-Arg-Phe-4Pal-DTrp-Lys-Thr-Tyr);

Compound 12: DTyr-cyclo(DLys-Arg-Phe-Phe-DTrp-Lys-Thr-4FPhe);

Compound 17: Tyr-cyclo(DLys-Arg-Phe-4Pal-DTrp-Lys-Thr-Phe);

Compound 18: Tyr-cyclo(DLys-Arg-Phe-Phe-DTrp-Lys-Thr-Phe);

Compound 19: Tyr-cyclo(DLys-Arg-Phe-4Pal-DTrp-Lys-Thr-Tyr);

Compound 20: Tyr-cyclo(DLys-Arg-Phe-Phe-DTrp-Lys-Thr-4FPhe); and

Compound 21: Tyr-psi(CH$_2$NH)-cyclo(DLys-Arg-Phe-4Pal-DTrp-Lys-Thr-Phe).

The compound according to another preferred embodiment of the present invention comprises a compound selected from the following list:

Compound 1: cyclo(DLys-Arg-Phe-4Pal-DTrp-Lys-Thr-Phe);

Compound 2: cyclo(DLys-Arg-Phe-Phe-DTrp-Lys-Thr-Phe);

Compound 3: cyclo(DLys-Arg-Phe-4Pal-DTrp-Lys-Thr-Tyr); and

Compound 4: cyclo(DLys-Arg-Phe-Phe-DTrp-Lys-Thr-4FPhe).

The compound according to another preferred embodiment of the present invention comprises a compound selected from the following list:

Compound 5: 1-[(ethan-2-oyl)-Tyr-psi(CH$_2$NH)-cyclo(DLys-Arg-Phe-4Pal-DTrp-Lys-Thr-Phe)],4-[(propan-3-oyl)-Tyr-psi(CH$_2$NH)-cyclo(DLys-Arg-Phe-4Pal-DTrp-Lys-Thr-Phe)]-1,2,3-triazole;

Compound 6: 1-[(ethan-2-oyl)-Tyr-psi(CH$_2$NH)-cyclo(DLys-Arg-Phe-Phe-DTrp-Lys-Thr-4FPhe)],4-[(propan-3-oyl)-Tyr-psi(CH$_2$NH)-cyclo(DLys-Arg-Phe-Phe-DTrp-Lys-Thr-4FPhe)]-1,2,3-triazole; and Compound 7: 1-[(ethan-2-oyl)-Tyr-psi(CH$_2$NH)-cyclo(DLys-Arg-Phe-Phe-DTrp-Lys-Thr-Tyr)],4-[(propan-3-oyl)-Tyr-psi(CH$_2$NH)-cyclo(DLys-Arg-Phe-Phe-DTrp-Lys-Thr-Tyr)]-1,2,3-triazole.

Additionally, the present invention provides a method of treating a disease or condition in a subject, said method comprising administering to said subject a therapeutically effective amount of a compound described herein, or a pharmaceutically acceptable salt thereof, wherein said disease or disorder is selected from the list consisting of: Cushing's syndrome, gonadotropinoma, hyperparathyroidism, Paget's disease, VIPoma, nesidioblastosis, hyperinsulinism, gastrinoma, Zollinger-Ellison syndrome, hypersecretory diarrhea related to AIDS and other conditions, irritable bowel syndrome, pancreatitis, Crohn's disease, systemic sclerosis, thyroid cancer, psoriasis, hypotension, panic attacks, sclerodoma, small bowel obstruction, gastroesophageal reflux, duodenogastric reflux, Graves' disease, polycystic ovary disease, upper gastrointestinal bleeding, pancreatic pseudocysts, pancreatic ascites, leukemia, meningioma, cancer cachexia, acromegaly, restenosis, hepatoma, lung cancer, melanoma, inhibiting the accelerated growth of a solid tumor, decreasing body weight, treating insulin resistance, Syndrome X, prolonging the survival of pancreatic cells, fibrosis, hyperlipidemia, hyperamylinemia, hyperprolactinemia, prolactinomas, diabetic neuropathy, macular degeneration, hypercalcemia of malignancy, postprandial portal hypertension, and complications of portal hypertension.

Additionally, the present invention provides a method of treating a disease or condition in a subject, said method comprising administering to said subject a therapeutically effective amount of a compound described herein, or a pharmaceutically acceptable salt thereof, wherein said disease or disorder is selected from the list consisting of: acromegaly; endocrine pancreatic tumors, such as insulinomas and glucagonomas; ectopic tumors, such as gastrinomas; and vasoactive intestinal peptide (VIP)-producing tumors.

It is contemplated that the compounds of the present invention will be routinely combined with other active ingredients such as anticancer agents, antibiotics, antibodies, antiviral agents, analgesics (e.g., a nonsteroidal anti-inflammatory drug (NSAID), acetaminophen, opioids, COX-2 inhibitors), immunostimulatory agents (e.g., cytokines or a synthetic immunostimulatory organic molecules), hormones (natural, synthetic, or semisynthetic), central nervous system (CNS) stimulants, antiemetic agents, antihistamines, erythropoietin, agents that activate complement, sedatives, muscle relaxants, anesthetic agents, anticonvulsive agents, antidepressants, antipsychotic agents, GH antagonists, radiotherapies, chemotherapies, and combinations thereof.

The compounds of the instant invention generally can be provided in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts can be formed by taking about 1 equivalent of a compound of the invention and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention features pharmaceutical compositions comprising, as an active ingredient, at least one compound of the invention in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

In general, an effective dose of an active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

Preferred dosage ranges are from 0.01 to 10.0 mg/kg of body weight. Such dosages may be administered, for example, daily as a single dose or divided into multiple doses.

Further, the compounds of the invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. The teachings of the foregoing patents and applications are incorporated herein by reference.

The use of immediate or of sustained release compositions depends on the type of indications targeted. If the indication consists of an acute or over-acute disorder, a treatment with an immediate form will be preferred over the same with a prolonged release composition. On the contrary, for preventive or long-term treatments, a prolonged release composition will generally be preferred.

Synthesis of Somatostatin Agonists

The methods for synthesizing peptide somatostatin agonists are well documented and are within the ability of a person of ordinary skill in the art. For example, peptides may be synthesized on Rink amide MBHA resin (4-(2'4'-dimethoxyphenyl-Fmoc-aminomethyl)-phenoxyacetamido-norleucyl-MBHA resin) using a standard solid phase protocol of Fmoc chemistry.

The synthesis of somatostatin agonists with a substituted N-terminus can be achieved, for example, by following the protocol set forth in PCT publication No. WO 94/04752.

Synthesis of somatostatin agonists with a lactam bridge is described in PCT publication No. WO 03/014158.

Certain uncommon amino acids were purchased from the following vendors: Fmoc-Doc-OH and Fmoc-Aepa-OH were purchased from Chem-Impex Int'l Inc. (Wood Dale, Ill., USA).

The following examples are provided to illustrate the invention. They are not meant to limit the invention in any way.

EXAMPLES

Synthetic Procedure for DTyr-cyclo(DLys-Arg-Phe-Phe-DTrp-Lys-Thr-4FPhe) (Compound 12)

The titled peptide was prepared with Symphony® synthesizer (Protein Technologies, Inc., Tucson, Ariz., USA) on a 0.2 mmole scale (2×0.1 mmol each reaction vessel) starting with Fmoc-4FPhe-ClTrt resin (0.825 mmole/g, 122 mg). The resin was swelled in DMF for 3×10 minutes. The deprotections were done using 20% piperidine in DMF. The double couplings were done using 0.9 eq. of HCTU as a coupling agent. The following amino acids were added successively: Fmoc-Thr(tBu)-OH, Fmoc-Lys(Boc)-OH, Fmoc-DTrp(Boc)-OH, Fmoc-Phe-OH, Fmoc-Phe-OH, Fmoc-Arg(Pbf)-OH, Fmoc-DLys(Mtt)-OH, and Fmoc-DTyr(tBu)-OH, based on the protocol of the synthesizer. After the coupling of Fmoc-DTyr(tBu)-OH was completed, the Fmoc was removed using 20% piperidine in DMF. The resin was mixed with a DMF solution of (Boc)$_2$O (4 eq.) and DIEA (2 eq.) for 2 hours.

After washing with DCM, the resin was treated with 32 mL of solution (32 mL for 0.159 mmol scale resin) containing TFA/DCM (1/99) for 30 minutes, then filtered into 0.583 mL of TEA and evaporated to dryness. This process was repeated another 3 times. The crude linear product was dissolved in 77.5 mL of DCM, to which 2 eq. of PyAOP, 2.5 eq. of HOBt and 16 eq. of DIEA were added. The lactam formation was monitored by HPLC.

The above cyclized protected crude product was treated with a solution of TFA/TIS/H$_2$O/DTT (20 mL/1.26 mL/1.34 mL/1.25 g) for 6 hours and filtered in 150 mL of cold ether. After centrifugation, the precipitate was ready for purification.

The crude product was dissolved in water. Acetonitrile was added dropwise to make clear solution if needed. It was purified on a reverse-phase preparative Waters HPLC/MS using a Luna C18 column from Phenomenex (100×21.2 mm, 100 Å, 5 μm). The peptide was eluted from the column with a gradient from 10-30% B in 35 minutes, where A was 0.1% TFA in water and B was 0.1% TFA in acetonitrile. The fractions were checked on ACQUITY UPLC™ (Waters Corporation; Milford, Mass., USA) and fractions containing pure product were combined and lyophilized to dryness. ESI-MS analysis was used to determine the molecular weight of the peptide. It generated 123.1 mg (98.8% yield based on 0.2 mmol scale). The product was found to be homogenous and the purity was 98.8% based on an analytical HPLC analysis. ESI-MS analysis gave the molecular weight of 1322.8 (in agreement with the calculated molecular weight of 1322.5).

Synthetic Procedure for Tyr-psi(CH$_2$NH)-cyclo(DLys-Arg-Phe-4Pal-DTrp-Lys-Thr-Phe) (Compound 21)

The titled peptide was prepared with Symphony® synthesizer (Protein Technologies, Inc., Tucson, Ariz., USA) on a 0.2 mmole scale (2×0.1 mmol each reaction vessel) starting with Fmoc-Phe-ClTrt resin (0.4699 mmole/g, 122 mg). The resin was swelled in DMF for 3×10 minutes. The deprotections were done using 20% piperidine in DMF. The double couplings were done using 0.9 eq. of HCTU as a coupling agent. The following amino acids were added successively: Fmoc-Thr(tBu)-OH, Fmoc-Lys(Boc)-OH, Fmoc-DTrp(Boc)-OH, Fmoc-4Pal-OH, Fmoc-Phe-OH, Fmoc-Arg(Pbf)-OH, and Fmoc-DLys(Mtt)-OH, based on the protocol of the synthesizer. The resin was capped and washed after each amino acid cycle. After the peptide assembly was complete, the resin was treated with 20% piperidine in DMF for half hour to remove the Fmoc protecting groups, and the resin was washed completely with DMF, MeOH and DCM. The resin with free NH$_2$ in 10 mL of DMF containing 1% AcOH was subjected to aminoalkylation with 4 eq. of Fmoc-Tyr(tBu)-CHO generated from reduction of Fmoc-Tyr(Bu)-weinreb amide using LAH/THF and 2.5 eq. of NaBH$_3$CN for overnight. After removal of Fmoc by 20% piperidine in DMF, the resin was mixed with a DMF solution of (Boc)$_2$O (4 eq.) and DIEA (2 eq.) for 2 hours.

The selective cleavage, lactam formation, global cleavage and purification were the same as those described for the synthesis of Compound 12. The product was found to be homogenous and the purity was 97.5% based on an analytical HPLC analysis. ESI-MS analysis gave the molecular weight of 1291.8 (in agreement with the calculated molecular weight of 1291.6).

Synthetic Procedure for 1-[(ethan-2-oyl)-Tyr-psi(CH$_2$NH)-cyclo(DLys-Arg-Phe-Phe-DTrp-Lys-Thr-4FPhe)],4-[(propan-3-oyl)-Tyr-psi(CH$_2$NH)-cyclo(DLys-Arg-Phe-Phe-DTrp-Lys-Thr-4FPhe)]-1,2,3-triazole (Compound 6)

The titled peptide is a dimer of Tyr-psi(CH$_2$NH)-cyclo(DLys-Arg-Phe-Phe-DTrp-Lys-Thr-4FPhe) through linkage of 1,2,3-triazole ring. After the peptide assembly and Fmoc-Tyr(tBu)-CHO aminoalkylation were competed (the procedures were the same as those described above), the resin was treated with 20% piperidine/DMF for 40 minutes to remove the Fmoc protecting groups and washed thoroughly by DMF, MeOH and DCM. Then it was divided into two parts, wherein one part was coupled with 2-azido acetic acid, and the other part was coupled with 4-pentynoic acid under standard coupling conditions. Each resin was subjected to selective cleavage, lactam formation, global cleavage and purification. Each pure peptide was mixed under click reaction using ascorbic acid and copper II acetate to form the final compound. After purification, the product was found to be homogenous and the purity was 97.4% based on an analytical HPLC analysis. ESI-MS analysis gave the molecular weight of 2780.8 (in agreement with the calculated molecular weight of 2780.3).

The physical data of select compounds according to the present invention are compiled in Table II.

TABLE II

| Compound No. | Molecular weight (calculated) | Molecular weight (ESI-MS) | Purity (%; HPLC) |
|---|---|---|---|
| 1 | 1142.4 | 1142.6 | 98.9 |
| 2 | 1141.4 | 1141.3 | 99.7 |
| 3 | 1158.4 | 1158.4 | 99.3 |
| 4 | 1159.4 | 1159.5 | 99.5 |
| 5 | 2746.3 | 2746.7 | 99.0 |
| 6 | 2780.3 | 2780.8 | 97.4 |
| 7 | 2776.3 | 2776.9 | 98.8 |
| 12 | 1322.5 | 1322.8 | 98.8 |
| 17 | 1305.5 | 1305.4 | 98.8 |
| 19 | 1321.5 | 1321.5 | 94.4 |
| 21 | 1291.6 | 1291.8 | 97.5 |
| 126 | 3356.9 | 3357.3 | 98.5 |

Somatostatin Receptor Radioligand Binding Assays

The affinities of a test compound for the human somatostatin receptors were determined by radioligand binding assays in CHO-K1 cells stably transfected with each of the somatostatin receptor subtypes, hSSTR1-5. The cDNA coding sequences of the hSSTR1 (GenBank accession No. NM_001049.1), hSSTR2 (GenBank accession No. XM_012697.1), hSSTR3 (GenBank accession No. XM_009963.1), hSSTR4 (GenBank accession No. NM_001052.1) and hSSTR5 (GenBank accession No. XM_012565.1) were subcloned into the mammalian expression vector pcDNA3.1 (Life Technologies). Clonal cell lines stably expressing each of the somatostatin receptors were obtained by transfection into CHO-K1 cells (ATCC) and subsequently selected with culture media containing 0.8 mg/mL of G418 (Life Technologies).

Membranes for in vitro receptor binding assays were obtained by the following procedures. CHO-K1 cells expressing one of the somatostatin receptors were homogenized in ice-cold buffer with 10 mM Tris-HCl, 5 mM EDTA, 3 mM EGTA, 1 mM phenylmethylsuphonyl fluoride, pH 7.6, using Polytron PT10-35GT (Kinematica) at 18,000 rpm for 30 seconds and centrifuged at 500×g for 10 minutes. The supernatant containing the plasma membranes was centrifuged at 100,000×g for 30 minutes and the pellet was resuspended in buffer containing 20 mM glycine-glycine, 1 mM $MgCl_2$, 250 mM sucrose, pH 7.2, for storage at −80° C.

For the hSSTR1, 2 and 5 assays, membranes and various concentrations of test compounds were incubated in 96-well plates for 60 minutes at 25° C. with 0.05 nM [$^{125}$I-Tyr$^{11}$]-SRIF-14 (for hSSTR1; PerkinElmer Life Science), 0.05 nM [$^{125}$I-Tyr]-seglitide (for hSSTR2; PerkinElmer Life Science) or 0.05 nM [$^{125}$I-Tyr]-DPhe-cyclo(Cys-Tyr-DTrp-Lys-Val-Cys)-Thr-$NH_2$ (for hSSTR5; PerkinElmer Life Science) in 50 mM HEPES, 0.2% BSA, 0.1 mM $MgCl_2$, pH 7.5.

For the hSSTR3 and 4 assays, membranes and various concentrations of test compounds were incubated in 96-well plates for 60 minutes at 25° C. with 0.05 nM [$^{125}$I-Tyr$^{11}$]-SRIF-14 (PerkinElmer Life Science) in 50 mM HEPES, 0.2% BSA, 5 mM $MgCl_2$, 200 KIU/mL trasylol, 0.02 mg/mL bacitracin, and 0.02 mg/mL phenylmethylsuphonyl fluoride, pH 7.5.

The incubations were terminated by rapid filtration through GF/C glass microfiber filter plates (pre-wet with 0.3% polyethyleneimine and 0.1% BSA) using a 96-well cell harvester (Brandel). Plates were washed six times with 1 mL/well aliquots of ice-cold buffer containing 50 mM Tris buffer, pH 7.7. Specific binding is defined as the total radioligand bound minus the bound in the presence of 1000 nM SRIF-14.

The results of the somatostatin receptor radioligand binding assays as described hereinabove are provided in Table III for select compounds according to the present invention.

TABLE III

| Compound No. | hSSTR1 Ki (nM) ± SEM | hSSTR2 Ki (nM) ± SEM | hSSTR3 Ki (nM) ± SEM | hSSTR4 Ki (nM) ± SEM | hSSTR5 Ki (nM) ± SEM |
|---|---|---|---|---|---|
| 1 | >1000 | 0.47 ± 0.03 | 16.3 ± 7.1 | 76.3 ± 12.6 | 0.31 ± 0.1 |
| 2 |  | 2.01 ± 1.14 |  |  |  |
| 3 | >1000 | 0.72 ± 0.28 | 21.6 ± 16.6 | 137.9 ± 5.3 | 0.32 ± 0.1 |
| 4 | 21.8 ± 4.7 | 1.54 ± 0.00 | 0.4 ± 0.3 | 18.4 ± 2.5 | 0.06 ± 0.0 |
| 5 |  | 0.08 |  |  |  |
| 6 |  | 0.38 |  |  |  |
| 7 |  | 0.17 |  |  |  |
| 12 |  | 0.86 ± 0.26 |  |  |  |
| 17 |  | 0.57 ± 0.14 |  |  |  |
| 19 |  | 0.52 ± 0.00 |  |  |  |
| 21 | 270.8 ± 160.1 | 0.02 ± 0.02 | 5.0 | 112.1 ± 18.6 | 0.32 |

Intracellular Calcium Mobilization Assays

The ability of select compounds according to the present invention to activate hSSTR2 was determined by the intracellular calcium mobilization assay using FLIPR Calcium 4 assay kit (Molecular Devices).

Cells expressing hSSTR2 were plated in 384-well microplates in tissue culture media and incubated for 16-24 hours at 37° C. in a humidified atmosphere with 5% $CO_2$. Medium was replaced by loading buffer containing Hank's buffered saline, 20 mM HEPES, 2.5 mM probenecid and Calcium 4 dye, and the plates were incubated at 37° C. for 60 minutes. Various concentrations of the test compounds were applied to the cells during the fluorescence measurement with excitation at 485 nm and emission at 525 nm using the Flexstation III microplate reader (Molecular Devices).

The half maximal effective concentrations ($EC_{50}$) were calculated by fitting data to sigmoid dose-response curves using GraphPad Prism version 5.03 (GraphPad Software, San Diego, Calif., USA). % $E_{max}$ values represent the maximal effect of the test compound in percentage of the maximal effect of SRIF-14.

The results of the intracellular calcium mobilization assays as described hereinabove are provided in Table IV for select compounds according to the present invention.

TABLE IV

| | hSSTR2 | |
|---|---|---|
| Compound No. | $EC_{50}$ (nM) ± SEM | % $E_{max}$ ± SEM |
| 1 | 9.1 ± 3.9 | 96.3 ± 5.5 |
| 2 | 17.1 ± 7.8 | 87.4 ± 6.1 |
| 3 | 31.8 ± 12.4 | 97.5 ± 4.2 |
| 4 | 28.4 ± 18.5 | 97.1 ± 0.6 |
| 5 | 3.3 ± 0.0 | 88.6 ± 1.1 |
| 6 | 74.6 ± 15.6 | 93.6 ± 4.1 |
| 7 | 28.5 ± 11.5 | 97.4 ± 1.2 |
| 12 | 28.8 ± 0.3 | 103.7 ± 1.0 |
| 17 | 62.0 ± 10.7 | 96.7 ± 9.0 |
| 19 | 55.5 ± 8.0 | 101.2 ± 2.5 |
| 21 | 4.4 ± 3.7 | 103.0 ± 0.2 |

Reference Compound No. A, whose chemical name and corresponding structure are provided in Table V, was synthesized and its ability to activated hSSTR2 was determined by the same intracellular calcium mobilization assays using FLIPR Calcium 4 assay kit (Molecular Devices) and under the same experimental conditions for the test compounds, as described hereinabove, and the results thereof are provided in Table VI.

TABLE V

| Reference Compound No. | Chemical Name; Corresponding Structure |
| --- | --- |
| A | H-Tyr-cyclo(DDab-Arg-Phe-Phe-DTrp-Lys-Thr-Phe); |

TABLE VI

| Reference Compound No. | hSSTR2 | |
| --- | --- | --- |
| | EC$_{50}$ (nM) ± SEM | % E$_{max}$ ± SEM |
| A | 15.9 ± 3.1 | 64.1 ± 4.3 |

In the chemical name as listed in Table V, the term "Dab" is an abbreviation for an amino acid residue 2,4-diaminobutyric acid.

Referring to Tables IV and VI, the compounds of the invention all showed activity at hSSTR2 and compared favorably to Reference Compound No. A, showing statistically significant improvement in EC$_{50}$ and/or % E$_{max}$.

All publications, patent applications, patents, and other documents cited herein are incorporated by reference in their entirety. In case of conflict, the present specification, including definitions, will control. In addition, the materials, methods, and examples are illustrative only and not intended to be limiting.

Obvious variations to the disclosed compounds and alternative embodiments of the invention will be apparent to those skilled in the art in view of the foregoing disclosure. All such obvious variants and alternatives are considered to be within the scope of the invention as described herein.

The invention claimed is:

1. A compound according to Formula I, $$A^1\text{-cyclo(DLys-Arg-Phe-}A^5\text{-DTrp-Lys-Thr-}A^9) \quad (I)$$

wherein:
A$^1$ is DTyr, Tyr, DLys, Lys, D2Nal, 2Nal, D1Nal, 1Nal, or absent;
A$^5$ is Phe, 2Pal, 3Pal, or 4Pal;
A$^9$ is Phe, 2FPhe, 3FPhe, 4FPhe, 3,4FPhe, 3,5FPhe, 2,3,4,5,6FPhe, or Tyr; and
A$^1$ is optionally acylated with RC(O), wherein R is C$_{1-10}$ alkyl;
or a pharmaceutically acceptable salt thereof.

2. The compound according to claim 1, wherein said compound is:

cyclo(DLys-Arg-Phe-4Pal-DTrp-Lys-Thr-Phe);
cyclo(DLys-Arg-Phe-Phe-DTrp-Lys-Thr-Phe);
cyclo(DLys-Arg-Phe-4Pal-DTrp-Lys-Thr-Tyr);
cyclo(DLys-Arg-Phe-Phe-DTrp-Lys-Thr-4FPhe);
DTyr-cyclo(DLys-Arg-Phe-Phe-DTrp-Lys-Thr-Phe);
DTyr-cyclo(DLys-Arg-Phe-4Pal-DTrp-Lys-Thr-Tyr);
DTyr-cyclo(DLys-Arg-Phe-Phe-DTrp-Lys-Thr-4FPhe);
Tyr-cyclo(DLys-Arg-Phe-4Pal-DTrp-Lys-Thr-Phe);
Tyr-cyclo(DLys-Arg-Phe-Phe-DTrp-Lys-Thr-Phe);
Tyr-cyclo(DLys-Arg-Phe-4Pal-DTrp-Lys-Thr-Tyr);
Tyr-cyclo(DLys-Arg-Phe-Phe-DTrp-Lys-Thr-4FPhe);
D2Nal-cyclo(DLys-Arg-Phe-4Pal-DTrp-Lys-Thr-Phe);
D2Nal-cyclo(DLys-Arg-Phe-Phe-DTrp-Lys-Thr-Phe);
D2Nal-cyclo(DLys-Arg-Phe-4Pal-DTrp-Lys-Thr-Tyr);
D2Nal-cyclo(DLys-Arg-Phe-Phe-DTrp-Lys-Thr-4FPhe);
2Nal-cyclo(DLys-Arg-Phe-4Pal-DTrp-Lys-Thr-Phe);
2Nal-cyclo(DLys-Arg-Phe-Phe-DTrp-Lys-Thr-Phe);
2Nal-cyclo(DLys-Arg-Phe-4Pal-DTrp-Lys-Thr-Tyr);
2Nal-cyclo(DLys-Arg-Phe-Phe-DTrp-Lys-Thr-4FPhe);
D1Nal-cyclo(DLys-Arg-Phe-4Pal-DTrp-Lys-Thr-Phe);
D1Nal-cyclo(DLys-Arg-Phe-Phe-DTrp-Lys-Thr-Phe);
D1Nal-cyclo(DLys-Arg-Phe-4Pal-DTrp-Lys-Thr-Tyr);
D1Nal-cyclo(DLys-Arg-Phe-Phe-DTrp-Lys-Thr-4FPhe);
1Nal-cyclo(DLys-Arg-Phe-4Pal-DTrp-Lys-Thr-Phe);
1Nal-cyclo(DLys-Arg-Phe-Phe-DTrp-Lys-Thr-Phe);
1Nal-cyclo(DLys-Arg-Phe-4Pal-DTrp-Lys-Thr-Tyr);
1Nal-cyclo(DLys-Arg-Phe-Phe-DTrp-Lys-Thr-4FPhe); or
DTyr-cyclo(DLys-Arg-Phe-4Pal-DTrp-Lys-Thr-Phe);
or a pharmaceutically acceptable salt thereof.

3. A compound according to Formula Ia, $$A^1\text{-B-cyclo(DLys-Arg-Phe-}A^5\text{-DTrp-Lys-Thr-}A^9) \quad (Ia)$$

wherein:
A$^1$ is DTyr, Tyr, DLys, Lys, D2Nal, 2Nal, D1Nal, 1Nal, or absent;
B is a pseudopeptide bond;
A$^5$ is Phe, 2Pal, 3Pal, or 4Pal; and
A$^9$ is Phe, 2FPhe, 3FPhe, 4FPhe, 3,4FPhe, 3,5FPhe, 2,3,4,5,6FPhe, or Tyr; and A¹ is optionally acylated with RC(O), wherein R is $C_{1-10}$ alkyl;

or a pharmaceutically acceptable salt thereof.

4. The compound according to claim 3, wherein said pseudopeptide bond is psi(CH₂NR), wherein R is H, $(C_{1-10})$alkyl, substituted $(C_{1-10})$alkyl, $(C_{1-10})$heteroalkyl, substituted $(C_{1-10})$heteroalkyl, $(C_{2-10})$alkenyl, substituted $(C_{2-10})$alkenyl, $(C_{2-10})$alkynyl, substituted $(C_{2-10})$alkynyl, aryl, alkylaryl, substituted alkylaryl, arylalkyl, substituted arylalkyl, $(C_{2-10})$acyl, or substituted $(C_{2-10})$acyl; or a pharmaceutically acceptable salt thereof.

5. The compound according to claim 4, wherein said pseudopeptide bond is psi(CH₂NH); or a pharmaceutically acceptable salt thereof.

6. The compound according to claim 5, wherein said compound is:
DTyr-psi(CH₂NH)-cyclo(DLys-Arg-Phe-4Pal-DTrp-Lys-Thr-Phe);
DTyr-psi(CH₂NH)-cyclo(DLys-Arg-Phe-Phe-DTrp-Lys-Thr-Phe);
DTyr-psi(CH₂NH)-cyclo(DLys-Arg-Phe-4Pal-DTrp-Lys-Thr-Tyr);
DTyr-psi(CH₂NH)-cyclo(DLys-Arg-Phe-Phe-DTrp-Lys-Thr-4FPhe);
Tyr-psi(CH₂NH)-cyclo(DLys-Arg-Phe-4Pal-DTrp-Lys-Thr-Phe);
Tyr-psi(CH₂NH)-cyclo(DLys-Arg-Phe-Phe-DTrp-Lys-Thr-Phe);
Tyr-psi(CH₂NH)-cyclo(DLys-Arg-Phe-4Pal-DTrp-Lys-Thr-Tyr);
Tyr-psi(CH₂NH)-cyclo(DLys-Arg-Phe-Phe-DTrp-Lys-Thr-4FPhe);
D2Nal-psi(CH₂NH)-cyclo(DLys-Arg-Phe-4Pal-DTrp-Lys-Thr-Phe);
D2Nal-psi(CH₂NH)-cyclo(DLys-Arg-Phe-Phe-DTrp-Lys-Thr-Phe);
D2Nal-psi(CH₂NH)-cyclo(DLys-Arg-Phe-4Pal-DTrp-Lys-Thr-Tyr);
D2Nal-psi(CH₂NH)-cyclo(DLys-Arg-Phe-Phe-DTrp-Lys-Thr-4FPhe);
2Nal-psi(CH₂NH)-cyclo(DLys-Arg-Phe-4Pal-DTrp-Lys-Thr-Phe);
2Nal-psi(CH₂NH)-cyclo(DLys-Arg-Phe-Phe-DTrp-Lys-Thr-Phe);
2Nal-psi(CH₂NH)-cyclo(DLys-Arg-Phe-4Pal-DTrp-Lys-Thr-Tyr);
2Nal-psi(CH₂NH)-cyclo(DLys-Arg-Phe-Phe-DTrp-Lys-Thr-4FPhe);
D1Nal-psi(CH₂NH)-cyclo(DLys-Arg-Phe-4Pal-DTrp-Lys-Thr-Phe);
D1Nal-psi(CH₂NH)-cyclo(DLys-Arg-Phe-Phe-DTrp-Lys-Thr-Phe);
D1Nal-psi(CH₂NH)-cyclo(DLys-Arg-Phe-4Pal-DTrp-Lys-Thr-Tyr);
D1Nal-psi(CH₂NH)-cyclo(DLys-Arg-Phe-Phe-DTrp-Lys-Thr-4FPhe);
1Nal-psi(CH₂NH)-cyclo(DLys-Arg-Phe-4Pal-DTrp-Lys-Thr-Phe);
1Nal-psi(CH₂NH)-cyclo(DLys-Arg-Phe-Phe-DTrp-Lys-Thr-Phe);
1Nal-psi(CH₂NH)-cyclo(DLys-Arg-Phe-4Pal-DTrp-Lys-Thr-Tyr);
1Nal-psi(CH₂NH)-cyclo(DLys-Arg-Phe-Phe-DTrp-Lys-Thr-4FPhe); or
Tyr-psi(CH₂NH)-cyclo(DLys-Arg-Phe-Phe-DTrp-Lys-Thr-Tyr);
or a pharmaceutically acceptable salt thereof.

7. A compound according to Formula II,

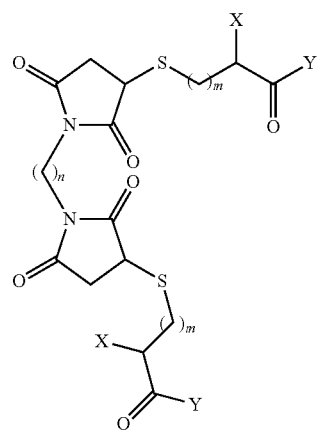

(II)

wherein:
n is 1-10;
m is 1-6;
X is H, H₂N, or Ac—HN; and
Y is, independent for each occurrence, a compound according to: Formula I, $$A^1\text{-cyclo}(DLys\text{-}Arg\text{-}Phe\text{-}A^5\text{-}DTrp\text{-}Lys\text{-}Thr\text{-}A^9) \quad (I)$$

wherein:
A¹ is DTyr, Tyr, DLys, Lys, D2Nal, 2Nal, D1Nal, 1Nal, or absent;
A⁵ is Phe, 2Pal, 3Pal, or 4 Pal; and
A⁹ is Phe, 2FPhe, 3FPhe, 4FPhe, 3,4FPhe, 3,5FPhe, 2,3,4,5,6FPhe, or Tyr; or Formula Ia, $$A^1\text{-}B\text{-cyclo}(DLys\text{-}Arg\text{-}Phe\text{-}A^5\text{-}DTrp\text{-}Lys\text{-}Thr\text{-}A^9) \quad (Ia)$$

wherein:
A¹ is DTyr, Tyr, DLys, Lys, D2Nal, 2Nal, D1Nal, 1Nal, or absent;
B is a pseudopeptide bond;
A⁵ is Phe, 2Pal, 3Pal, or 4 Pal; and
A⁹ is Phe, 2FPhe, 3FPhe, 4FPhe, 3,4FPhe, 3,5FPhe, 2,3,4,5,6FPhe, or Tyr;
or a pharmaceutically acceptable salt thereof.

8. A compound according to Formula III,

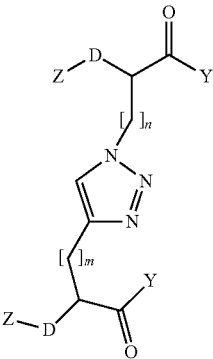

(III)

wherein:
Z is, independent for each occurrence, H or CH₃—(CH₂)ₛ—C(O)—;

D is, independent for each occurrence, NH or absent;
s is 0-17;
each of m and n is, independent for each occurrence, 0-6; and
Y is, independent for each occurrence, a compound according to: Formula I, A$^1$-cyclo(DLys-Arg-Phe-A$^5$-DTrp-Lys-Thr-A$^9$)    (I)

wherein:
A$^1$ is DTyr, Tyr, DLys, Lys, D2Nal, 2Nal, D1Nal, 1Nal, or absent;
A$^5$ is Phe, 2Pal, 3Pal, or 4 Pal; and
A$^9$ is Phe, 2FPhe, 3FPhe, 4FPhe, 3,4FPhe, 3,5FPhe, 2,3,4,5,6FPhe, or Tyr; or Formula Ia, A$^1$-B-cyclo(DLys-Arg-Phe-A$^5$-DTrp-Lys-Thr-A$^9$)    (Ia)

wherein:
A$^1$ is DTyr, Tyr, DLys, Lys, D2Nal, 2Nal, D1Nal, 1Nal, or absent;
B is a pseudopeptide bond;
A$^5$ is Phe, 2Pal, 3Pal, or 4 Pal; and
A$^9$ is Phe, 2FPhe, 3FPhe, 4FPhe, 3,4FPhe, 3,5FPhe, 2,3,4,5,6FPhe, or Tyr;
or a pharmaceutically acceptable salt thereof.

9. The compound according to claim 8, wherein said compound is:
1-[(ethan-2-oyl)-Tyr-psi(CH$_2$NH)-cyclo(DLys-Arg-Phe-4Pal-DTrp-Lys-Thr-Phe)],4-[(propan-3-oyl)-Tyr-psi(CH$_2$NH)-cyclo(DLys-Arg-Phe-4Pal-DTrp-Lys-Thr-Phe)]-1,2,3-triazole;
1-[(ethan-2-oyl)-Tyr-psi(CH$_2$NH)-cyclo(DLys-Arg-Phe-Phe-DTrp-Lys-Thr-4FPhe)],4-[(propan-3-oyl)-Tyr-psi(CH$_2$NH)-cyclo(DLys-Arg-Phe-Phe-DTrp-Lys-Thr-4FPhe)]-1,2,3-triazole;
1-[(ethan-2-oyl)-Tyr-psi(CH$_2$NH)-cyclo(DLys-Arg-Phe-Phe-DTrp-Lys-Thr-Tyr)],4-[(propan-3-oyl)-Tyr-psi(CH$_2$NH)-cyclo(DLys-Arg-Phe-Phe-DTrp-Lys-Thr-Tyr)]-1,2,3-triazole;
1-[(ethan-2-oyl)-Tyr-psi(CH$_2$NH)-cyclo(DLys-Arg-Phe-Phe-DTrp-Lys-Thr-Phe)],4-[(propan-3-oyl)-Tyr-psi(CH$_2$NH)-cyclo(DLys-Arg-Phe-Phe-DTrp-Lys-Thr-Phe)]-1,2,3-triazole;
1-[(ethan-2-oyl)-Tyr-psi(CH$_2$NH)-cyclo(DLys-Arg-Phe-4Pal-DTrp-Lys-Thr-Tyr)],4-[(propan-3-oyl)-Tyr-psi(CH$_2$NH)-cyclo(DLys-Arg-Phe-4Pal-DTrp-Lys-Thr-Tyr)]-1,2,3-triazole;
1-[(ethan-2-oyl)-cyclo(DLys-Arg-Phe-4Pal-DTrp-Lys-Thr-Phe)],4-[(propan-3-oyl)-cyclo(DLys-Arg-Phe-4Pal-DTrp-Lys-Thr-Phe)]-1,2,3-triazole;
1-[(ethan-2-oyl)-cyclo(DLys-Arg-Phe-Phe-DTrp-Lys-Thr-Phe)],4-[(propan-3-oyl)-cyclo(DLys-Arg-Phe-Phe-DTrp-Lys-Thr-Phe)]-1,2,3-triazole;
1-[(ethan-2-oyl)-cyclo(DLys-Arg-Phe-4Pal-DTrp-Lys-Thr-Tyr)],4-[(propan-3-oyl)-cyclo(DLys-Arg-Phe-4Pal-DTrp-Lys-Thr-Tyr)]-1,2,3-triazole;
1-[(ethan-2-oyl)-cyclo(DLys-Arg-Phe-Phe-DTrp-Lys-Thr-4FPhe)],4-[(propan-3-oyl)-cyclo(DLys-Arg-Phe-Phe-DTrp-Lys-Thr-4FPhe)]-1,2,3-triazole;
1-[(ethan-2-oyl)-DTyr-cyclo(DLys-Arg-Phe-4Pal-DTrp-Lys-Thr-Phe)],4-[(propan-3-oyl)-DTyr-cyclo(DLys-Arg-Phe-4Pal-DTrp-Lys-Thr-Phe)]-1,2,3-triazole;
1-[(ethan-2-oyl)-DTyr-cyclo(DLys-Arg-Phe-Phe-DTrp-Lys-Thr-Phe)],4-[(propan-3-oyl)-DTyr-cyclo(DLys-Arg-Phe-Phe-DTrp-Lys-Thr-Phe)]-1,2,3-triazole;
1-[(ethan-2-oyl)-DTyr-cyclo(DLys-Arg-Phe-4Pal-DTrp-Lys-Thr-Tyr)],4-[(propan-3-oyl)-DTyr-cyclo(DLys-Arg-Phe-4Pal-DTrp-Lys-Thr-Tyr)]-1,2,3-triazole;
1-[(ethan-2-oyl)-DTyr-cyclo(DLys-Arg-Phe-Phe-DTrp-Lys-Thr-4FPhe)],4-[(propan-3-oyl)-DTyr-cyclo(DLys-Arg-Phe-Phe-DTrp-Lys-Thr-4FPhe)]-1,2,3-triazole;
1-[(ethan-2-oyl)-DTyr-psi(CH$_2$NH)-cyclo(DLys-Arg-Phe-4Pal-DTrp-Lys-Thr-Phe)],4-[(propan-3-oyl)-DTyr-psi(CH$_2$NH)-cyclo(DLys-Arg-Phe-4Pal-DTrp-Lys-Thr-Phe)]-1,2,3-triazole;
1-[(ethan-2-oyl)-DTyr-psi(CH$_2$NH)-cyclo(DLys-Arg-Phe-Phe-DTrp-Lys-Thr-Phe)],4-[(propan-3-oyl)-DTyr-psi(CH$_2$NH)-cyclo(DLys-Arg-Phe-Phe-DTrp-Lys-Thr-Phe)]-1,2,3-triazole;
1-[(ethan-2-oyl)-DTyr-psi(CH$_2$NH)-cyclo(DLys-Arg-Phe-4Pal-DTrp-Lys-Thr-Tyr)],4-[(propan-3-oyl)-DTyr-psi(CH$_2$NH)-cyclo(DLys-Arg-Phe-4Pal-DTrp-Lys-Thr-Tyr)]-1,2,3-triazole;
1-[(ethan-2-oyl)-DTyr-psi(CH$_2$NH)-cyclo(DLys-Arg-Phe-Phe-DTrp-Lys-Thr-4FPhe)],4-[(propan-3-oyl)-DTyr-psi(CH$_2$NH)-cyclo(DLys-Arg-Phe-Phe-DTrp-Lys-Thr-4FPhe)]-1,2,3-triazole;
1-[(ethan-2-oyl)-Tyr-cyclo(DLys-Arg-Phe-4Pal-DTrp-Lys-Thr-Phe)],4-[(propan-3-oyl)-Tyr-cyclo(DLys-Arg-Phe-4Pal-DTrp-Lys-Thr-Phe)]-1,2,3-triazole;
1-[(ethan-2-oyl)-Tyr-cyclo(DLys-Arg-Phe-Phe-DTrp-Lys-Thr-Phe)],4-[(propan-3-oyl)-Tyr-cyclo(DLys-Arg-Phe-Phe-DTrp-Lys-Thr-Phe)]-1,2,3-triazole;
1-[(ethan-2-oyl)-Tyr-cyclo(DLys-Arg-Phe-4Pal-DTrp-Lys-Thr-Tyr)],4-[(propan-3-oyl)-Tyr-cyclo(DLys-Arg-Phe-4Pal-DTrp-Lys-Thr-Tyr)]-1,2,3-triazole;
1-[(ethan-2-oyl)-Tyr-cyclo(DLys-Arg-Phe-Phe-DTrp-Lys-Thr-4FPhe)],4-[(propan-3-oyl)-Tyr-cyclo(DLys-Arg-Phe-Phe-DTrp-Lys-Thr-4FPhe)]-1,2,3-triazole;
1-[(ethan-2-oyl)-D2Nal-cyclo(DLys-Arg-Phe-4Pal-DTrp-Lys-Thr-Phe)],4-[(propan-3-oyl)-D2Nal-cyclo(DLys-Arg-Phe-4Pal-DTrp-Lys-Thr-Phe)]-1,2,3-triazole;
1-[(ethan-2-oyl)-D2Nal-cyclo(DLys-Arg-Phe-Phe-DTrp-Lys-Thr-Phe)],4-[(propan-3-oyl)-D2Nal-cyclo(DLys-Arg-Phe-Phe-DTrp-Lys-Thr-Phe)]-1,2,3-triazole;
1-[(ethan-2-oyl)-D2Nal-cyclo(DLys-Arg-Phe-4Pal-DTrp-Lys-Thr-Tyr)],4-[(propan-3-oyl)-D2Nal-cyclo(DLys-Arg-Phe-4Pal-DTrp-Lys-Thr-Tyr)]-1,2,3-triazole;
1-[(ethan-2-oyl)-D2Nal-cyclo(DLys-Arg-Phe-Phe-DTrp-Lys-Thr-4FPhe)],4-[(propan-3-oyl)-D2Nal-cyclo(DLys-Arg-Phe-Phe-DTrp-Lys-Thr-4FPhe)]-1,2,3-triazole;
1-[(ethan-2-oyl)-D2Nal-psi(CH$_2$NH)-cyclo(DLys-Arg-Phe-4Pal-DTrp-Lys-Thr-Phe)],4-[(propan-3-oyl)-D2Nal-psi(CH$_2$NH)-cyclo(DLys-Arg-Phe-4Pal-DTrp-Lys-Thr-Phe)]-1,2,3-triazole;
1-[(ethan-2-oyl)-D2Nal-psi(CH$_2$NH)-cyclo(DLys-Arg-Phe-Phe-DTrp-Lys-Thr-Phe)],4-[(propan-3-oyl)-D2Nal-psi(CH$_2$NH)-cyclo(DLys-Arg-Phe-Phe-DTrp-Lys-Thr-Phe)]-1,2,3-triazole;
1-[(ethan-2-oyl)-D2Nal-psi(CH$_2$NH)-cyclo(DLys-Arg-Phe-4Pal-DTrp-Lys-Thr-Tyr)],4-[(propan-3-oyl)-D2Nal-psi(CH$_2$NH)-cyclo(DLys-Arg-Phe-4Pal-DTrp-Lys-Thr-Tyr)]-1,2,3-triazole;
1-[(ethan-2-oyl)-D2Nal-psi(CH$_2$NH)-cyclo(DLys-Arg-Phe-Phe-DTrp-Lys-Thr-4FPhe)],4-[(propan-3-oyl)-D2Nal-psi(CH$_2$NH)-cyclo(DLys-Arg-Phe-Phe-DTrp-Lys-Thr-4FPhe)]-1,2,3-triazole;
1-[(ethan-2-oyl)-D1Nal-cyclo(DLys-Arg-Phe-4Pal-DTrp-Lys-Thr-Phe)],4-[(propan-3-oyl)-D1Nal-cyclo(DLys-Arg-Phe-4Pal-DTrp-Lys-Thr-Phe)]-1,2,3-triazole;

1-[(ethan-2-oyl)-D1Nal-cyclo(DLys-Arg-Phe-Phe-DTrp-Lys-Thr-Phe)],4-[(propan-3-oyl)-D1Nal-cyclo(DLys-Arg-Phe-Phe-DTrp-Lys-Thr-Phe)]-1,2,3-triazole;

1-[(ethan-2-oyl)-D1Nal-cyclo(DLys-Arg-Phe-4Pal-DTrp-Lys-Thr-Tyr)],4-[(propan-3-oyl)-D1Nal-cyclo(DLys-Arg-Phe-4Pal-DTrp-Lys-Thr-Tyr)]-1,2,3-triazole;

1-[(ethan-2-oyl)-D1Nal-cyclo(DLys-Arg-Phe-Phe-DTrp-Lys-Thr-4FPhe)],4-[(propan-3-oyl)-D1Nal-cyclo(DLys-Arg-Phe-Phe-DTrp-Lys-Thr-4FPhe)]-1,2,3-triazole;

1-[(ethan-2-oyl)-D1Nal-psi(CH₂NH)-cyclo(DLys-Arg-Phe-4Pal-DTrp-Lys-Thr-Phe)],4-[(propan-3-oyl)-D1Nal-psi(CH₂NH)-cyclo(DLys-Arg-Phe-4Pal-DTrp-Lys-Thr-Phe)]-1,2,3-triazole;

1-[(ethan-2-oyl)-D1Nal-psi(CH₂NH)-cyclo(DLys-Arg-Phe-Phe-DTrp-Lys-Thr-Phe)],4-[(propan-3-oyl)-D1Nal-psi(CH₂NH)-cyclo(DLys-Arg-Phe-Phe-DTrp-Lys-Thr-Phe)]-1,2,3-triazole;

1-[(ethan-2-oyl)-D1Nal-psi(CH₂NH)-cyclo(DLys-Arg-Phe-4Pal-DTrp-Lys-Thr-Tyr)],4-[(propan-3-oyl)-D1Nal-psi(CH₂NH)-cyclo(DLys-Arg-Phe-4Pal-DTrp-Lys-Thr-Tyr)]-1,2,3-triazole; or 1-[(ethan-2-oyl)-D1Nal-psi(CH₂NH)-cyclo(DLys-Arg-Phe-Phe-DTrp-Lys-Thr-4FPhe)],4-[(propan-3-oyl)-D1Nal-psi(CH₂NH)-cyclo(DLys-Arg-Phe-Phe-DTrp-Lys-Thr-4FPhe)]-1,2,3-triazole;

or a pharmaceutically acceptable salt thereof.

10. A compound according to Formula IIIa, $$A^1\text{-cyclo(DLys-Arg-Phe-}A^5\text{-DTrp-Lys-Thr-}A^9) \quad \text{(IIIa)}$$

wherein:
Z is, independent for each occurrence, H or CH₃—(CH₂)$_s$—C(O)—;
D is, independent for each occurrence, NH or absent;
E is, independent for each occurrence, (Aepa)$_m$, (Doc)$_n$, —[C(O)—(CH₂)$_p$—C(O)]$_m$—, (Aepa)$_m$-(Doc)$_n$, (Doc)$_n$-(Aepa)$_m$, —[C(O)—(CH₂)$_p$—C(O)]$_m$-(Aepa)$_m$-(Doc)$_n$, —[C(O)—(CH₂)$_p$—C(O)]$_m$-(Doc)$_n$-(Aepa)$_m$, or absent;
s is 0-17;
each of m and n is, independent for each occurrence, 0-6;
p is 2-5; and
Y is, independent for each occurrence, a compound according to: Formula I, $$A^1\text{-cyclo(DLys-Arg-Phe-}A^5\text{-DTrp-Lys-Thr-}A^9) \quad \text{(I)}$$

wherein:
$A^1$ is DTyr, Tyr, DLys, Lys, D2Nal, 2Nal, D1Nal, 1Nal, or absent;
$A^5$ is Phe, 2Pal, 3Pal, or 4 Pal; and
$A^9$ is Phe, 2FPhe, 3FPhe, 4FPhe, 3,4FPhe, 3,5FPhe, 2,3,4,5,6FPhe, or Tyr; or Formula Ia, $$A^1\text{-B-cyclo(DLys-Arg-Phe-}A^5\text{-DTrp-Lys-Thr-}A^9) \quad \text{(Ia)}$$

wherein:
$A^1$ is DTyr, Tyr, DLys, Lys, D2Nal, 2Nal, D1Nal, 1Nal, or absent;
B is a pseudopeptide bond;
$A^5$ is Phe, 2Pal, 3Pal, or 4 Pal; and
$A^9$ is Phe, 2FPhe, 3FPhe, 4FPhe, 3,4FPhe, 3,5FPhe, 2,3,4,5,6FPhe, or Tyr;

or a pharmaceutically acceptable salt thereof.

11. The compound according to claim 10, wherein said compound is:

1-[(ethan-2-oyl)-Aepa-cyclo(DLys-Arg-Phe-4Pal-DTrp-Lys-Thr-Phe)],4-[(propan-3-oyl)-Aepa-cyclo(DLys-Arg-Phe-4Pal-DTrp-Lys-Thr-Phe)]-1,2,3-triazole;

1-[(ethan-2-oyl)-Aepa-cyclo(DLys-Arg-Phe-Phe-DTrp-Lys-Thr-Phe)],4-[(propan-3-oyl)-Aepa-cyclo(DLys-Arg-Phe-Phe-DTrp-Lys-Thr-Phe)]-1,2,3-triazole;

1-[(ethan-2-oyl)-Aepa-cyclo(DLys-Arg-Phe-4Pal-DTrp-Lys-Thr-Tyr)],4-[(propan-3-oyl)-Aepa-cyclo(DLys-Arg-Phe-4Pal-DTrp-Lys-Thr-Tyr)]-1,2,3-triazole;

1-[(ethan-2-oyl)-Aepa-cyclo(DLys-Arg-Phe-Phe-DTrp-Lys-Thr-4FPhe)],4-[(propan-3-oyl)-Aepa-cyclo(DLys-Arg-Phe-Phe-DTrp-Lys-Thr-4FPhe)]-1,2,3-triazole;

1-[(ethan-2-oyl)-Aepa-DTyr-cyclo(DLys-Arg-Phe-4Pal-DTrp-Lys-Thr-Phe)],4-[(propan-3-oyl)-Aepa-DTyr-cyclo(DLys-Arg-Phe-4Pal-DTrp-Lys-Thr-Phe)]-1,2,3-triazole;

1-[(ethan-2-oyl)-Aepa-DTyr-cyclo(DLys-Arg-Phe-Phe-DTrp-Lys-Thr-Phe)],4-[(propan-3-oyl)-Aepa-DTyr-cyclo(DLys-Arg-Phe-Phe-DTrp-Lys-Thr-Phe)]-1,2,3-triazole;

1-[(ethan-2-oyl)-Aepa-DTyr-cyclo(DLys-Arg-Phe-4Pal-DTrp-Lys-Thr-Tyr)],4-[(propan-3-oyl)-Aepa-DTyr-cyclo(DLys-Arg-Phe-4Pal-DTrp-Lys-Thr-Tyr)]-1,2,3-triazole;

1-[(ethan-2-oyl)-Aepa-DTyr-cyclo(DLys-Arg-Phe-Phe-DTrp-Lys-Thr-4FPhe)],4-[(propan-3-oyl)-Aepa-DTyr-cyclo(DLys-Arg-Phe-Phe-DTrp-Lys-Thr-4FPhe)]-1,2,3-triazole;

1-[(ethan-2-oyl)-Aepa-DTyr-psi(CH₂NH)-cyclo(DLys-Arg-Phe-4Pal-DTrp-Lys-Thr-Phe)],4-[(propan-3-oyl)-Aepa-DTyr-psi(CH₂NH)-cyclo(DLys-Arg-Phe-4Pal-DTrp-Lys-Thr-Phe)]-1,2,3-triazole;

1-[(ethan-2-oyl)-Aepa-DTyr-psi(CH₂NH)-cyclo(DLys-Arg-Phe-Phe-DTrp-Lys-Thr-Phe)],4-[(propan-3-oyl)-Aepa-DTyr-psi(CH₂NH)-cyclo(DLys-Arg-Phe-Phe-DTrp-Lys-Thr-Phe)]-1,2,3-triazole;

1-[(ethan-2-oyl)-Aepa-DTyr-psi(CH₂NH)-cyclo(DLys-Arg-Phe-4Pal-DTrp-Lys-Thr-Tyr)],4-[(propan-3-oyl)-Aepa-DTyr-psi(CH₂NH)-cyclo(DLys-Arg-Phe-4Pal-DTrp-Lys-Thr-Tyr)]-1,2,3-triazole;

1-[(ethan-2-oyl)-Aepa-DTyr-psi(CH₂NH)-cyclo(DLys-Arg-Phe-Phe-DTrp-Lys-Thr-4FPhe)],4-[(propan-3-oyl)-Aepa-DTyr-psi(CH₂NH)-cyclo(DLys-Arg-Phe-Phe-DTrp-Lys-Thr-4FPhe)]-1,2,3-triazole;

1-[(ethan-2-oyl)-Aepa-Tyr-cyclo(DLys-Arg-Phe-4Pal-DTrp-Lys-Thr-Phe)],4-[(propan-3-oyl)-Aepa-Tyr-cyclo(DLys-Arg-Phe-4Pal-DTrp-Lys-Thr-Phe)]-1,2,3-triazole;

1-[(ethan-2-oyl)-Aepa-Tyr-cyclo(DLys-Arg-Phe-Phe-DTrp-Lys-Thr-Phe)],4-[(propan-3-oyl)-Aepa-Tyr-cyclo(DLys-Arg-Phe-Phe-DTrp-Lys-Thr-Phe)]-1,2,3-triazole;

1-[(ethan-2-oyl)-Aepa-Tyr-cyclo(DLys-Arg-Phe-4Pal-DTrp-Lys-Thr-Tyr)],4-[(propan-3-oyl)-Aepa-Tyr-cyclo(DLys-Arg-Phe-4Pal-DTrp-Lys-Thr-Tyr)]-1,2,3-triazole;

1-[(ethan-2-oyl)-Aepa-Tyr-cyclo(DLys-Arg-Phe-Phe-DTrp-Lys-Thr-4FPhe)],4-[(propan-3-oyl)-Aepa-Tyr-cyclo(DLys-Arg-Phe-Phe-DTrp-Lys-Thr-4FPhe)]-1,2,3-triazole;

1-[(ethan-2-oyl)-Aepa-Tyr-psi(CH$_2$NH)-cyclo(DLys-Arg-Phe-4Pal-DTrp-Lys-Thr-Phe)],4-[(propan-3-oyl)-Aepa-Tyr-psi(CH$_2$NH)-cyclo(DLys-Arg-Phe-4Pal-DTrp-Lys-Thr-Phe)]-1,2,3-triazole;

1-[(ethan-2-oyl)-Aepa-Tyr-psi(CH$_2$NH)-cyclo(DLys-Arg-Phe-Phe-DTrp-Lys-Thr-Phe)],4-[(propan-3-oyl)-Aepa-Tyr-psi(CH$_2$NH)-cyclo(DLys-Arg-Phe-Phe-DTrp-Lys-Thr-Phe)]-1,2,3-triazole;

1-[(ethan-2-oyl)-Aepa-Tyr-psi(CH$_2$NH)-cyclo(DLys-Arg-Phe-4Pal-DTrp-Lys-Thr-Tyr)],4-[(propan-3-oyl)-Aepa-Tyr-psi(CH$_2$NH)-cyclo(DLys-Arg-Phe-4Pal-DTrp-Lys-Thr-Tyr)]-1,2,3-triazole;

1-[(ethan-2-oyl)-Aepa-Tyr-psi(CH$_2$NH)-cyclo(DLys-Arg-Phe-Phe-DTrp-Lys-Thr-4FPhe)],4-[(propan-3-oyl)-Aepa-Tyr-psi(CH$_2$NH)-cyclo(DLys-Arg-Phe-Phe-DTrp-Lys-Thr-4FPhe)]-1,2,3-triazole;

1-[(ethan-2-oyl)-Aepa-D2Nal-cyclo(DLys-Arg-Phe-4Pal-DTrp-Lys-Thr-Phe)],4-[(propan-3-oyl)-Aepa-D2Nal-cyclo(DLys-Arg-Phe-4Pal-DTrp-Lys-Thr-Phe)]-1,2,3-triazole;

1-[(ethan-2-oyl)-Aepa-D2Nal-cyclo(DLys-Arg-Phe-Phe-DTrp-Lys-Thr-Phe)],4-[(propan-3-oyl)-Aepa-D2Nal-cyclo(DLys-Arg-Phe-Phe-DTrp-Lys-Thr-Phe)]-1,2,3-triazole;

1-[(ethan-2-oyl)-Aepa-D2Nal-cyclo(DLys-Arg-Phe-4Pal-DTrp-Lys-Thr-Tyr)],4-[(propan-3-oyl)-Aepa-D2Nal-cyclo(DLys-Arg-Phe-4Pal-DTrp-Lys-Thr-Tyr)]-1,2,3-triazole;

1-[(ethan-2-oyl)-Aepa-D2Nal-cyclo(DLys-Arg-Phe-Phe-DTrp-Lys-Thr-4FPhe)],4-[(propan-3-oyl)-Aepa-D2Nal-cyclo(DLys-Arg-Phe-Phe-DTrp-Lys-Thr-4FPhe)]-1,2,3-triazole;

1-[(ethan-2-oyl)-Aepa-D2Nal-psi(CH$_2$NH)-cyclo(DLys-Arg-Phe-4Pal-DTrp-Lys-Thr-Phe)],4-[(propan-3-oyl)-Aepa-D2Nal-psi(CH$_2$NH)-cyclo(DLys-Arg-Phe-4Pal-DTrp-Lys-Thr-Phe)]-1,2,3-triazole;

1-[(ethan-2-oyl)-Aepa-D2Nal-psi(CH$_2$NH)-cyclo(DLys-Arg-Phe-Phe-DTrp-Lys-Thr-Phe)],4-[(propan-3-oyl)-Aepa-D2Nal-psi(CH$_2$NH)-cyclo(DLys-Arg-Phe-Phe-DTrp-Lys-Thr-Phe)]-1,2,3-triazole;

1-[(ethan-2-oyl)-Aepa-D2Nal-psi(CH$_2$NH)-cyclo(DLys-Arg-Phe-4Pal-DTrp-Lys-Thr-Tyr)],4-[(propan-3-oyl)-Aepa-D2Nal-psi(CH$_2$NH)-cyclo(DLys-Arg-Phe-4Pal-DTrp-Lys-Thr-Tyr)]-1,2,3-triazole;

1-[(ethan-2-oyl)-Aepa-D2Nal-psi(CH$_2$NH)-cyclo(DLys-Arg-Phe-Phe-DTrp-Lys-Thr-4FPhe)],4-[(propan-3-oyl)-Aepa-D2Nal-psi(CH$_2$NH)-cyclo(DLys-Arg-Phe-Phe-DTrp-Lys-Thr-4FPhe)]-1,2,3-triazole;

1-[(ethan-2-oyl)-Aepa-D1Nal-cyclo(DLys-Arg-Phe-4Pal-DTrp-Lys-Thr-Phe)],4-[(propan-3-oyl)-Aepa-D1Nal-cyclo(DLys-Arg-Phe-4Pal-DTrp-Lys-Thr-Phe)]-1,2,3-triazole;

1-[(ethan-2-oyl)-Aepa-D1Nal-cyclo(DLys-Arg-Phe-Phe-DTrp-Lys-Thr-Phe)],4-[(propan-3-oyl)-Aepa-D1Nal-cyclo(DLys-Arg-Phe-Phe-DTrp-Lys-Thr-Phe)]-1,2,3-triazole;

1-[(ethan-2-oyl)-Aepa-D1Nal-cyclo(DLys-Arg-Phe-4Pal-DTrp-Lys-Thr-Tyr)],4-[(propan-3-oyl)-Aepa-D1Nal-cyclo(DLys-Arg-Phe-4Pal-DTrp-Lys-Thr-Tyr)]-1,2,3-triazole;

1-[(ethan-2-oyl)-Aepa-D1Nal-cyclo(DLys-Arg-Phe-Phe-DTrp-Lys-Thr-4FPhe)],4-[(propan-3-oyl)-Aepa-D1Nal-cyclo(DLys-Arg-Phe-Phe-DTrp-Lys-Thr-4FPhe)]-1,2,3-triazole;

1-[(ethan-2-oyl)-Aepa-D1Nal-psi(CH$_2$NH)-cyclo(DLys-Arg-Phe-4Pal-DTrp-Lys-Thr-Phe)],4-[(propan-3-oyl)-Aepa-D1Nal-psi(CH$_2$NH)-cyclo(DLys-Arg-Phe-4Pal-DTrp-Lys-Thr-Phe)]-1,2,3-triazole;

1-[(ethan-2-oyl)-Aepa-D1Nal-psi(CH$_2$NH)-cyclo(DLys-Arg-Phe-Phe-DTrp-Lys-Thr-Phe)],4-[(propan-3-oyl)-Aepa-D1Nal-psi(CH$_2$NH)-cyclo(DLys-Arg-Phe-Phe-DTrp-Lys-Thr-Phe)]-1,2,3-triazole;

1-[(ethan-2-oyl)-Aepa-D1Nal-psi(CH$_2$NH)-cyclo(DLys-Arg-Phe-4Pal-DTrp-Lys-Thr-Tyr)],4-[(propan-3-oyl)-Aepa-D1Nal-psi(CH$_2$NH)-cyclo(DLys-Arg-Phe-4Pal-DTrp-Lys-Thr-Tyr)]-1,2,3-triazole;

1-[(ethan-2-oyl)-Aepa-D1Nal-psi(CH$_2$NH)-cyclo(DLys-Arg-Phe-Phe-DTrp-Lys-Thr-4FPhe)],4-[(propan-3-oyl)-Aepa-D1Nal-psi(CH$_2$NH)-cyclo(DLys-Arg-Phe-Phe-DTrp-Lys-Thr-4FPhe)]-1,2,3-triazole; or 1-[(ethan-2-oyl)-Doc-Doc-Tyr-psi(CH$_2$NH)-cyclo(DLys-Arg-Phe-Phe-DTrp-Lys-Thr-Tyr)],4-[(propan-3-oyl)-Doc-Doc-Tyr-psi(CH$_2$NH)-cyclo(DLys-Arg-Phe-Phe-DTrp-Lys-Thr-Tyr)]-1,2,3-triazole;

or a pharmaceutically acceptable salt thereof.

12. The compound according to claim 1 or 3, wherein $A^1$ is acylated with RC(O), wherein R is $C_{1-10}$ alkyl; or a pharmaceutically acceptable salt thereof.

13. The compound according to claim 12, wherein $A^1$ is acetylated; or a pharmaceutically acceptable salt thereof.

14. A pharmaceutical composition comprising an effective amount of the compound according to claim 1 or 3, or a pharmaceutically acceptable salt thereof, and a pharmaceutically acceptable carrier or diluent, wherein said effective amount is the amount effective to elicit a somatostatin receptor agonist effect in a subject in need thereof.

15. A method of treating a disease or condition in a human or other animal in need thereof, which comprises administering the compound according to claim 1 or 3, or a pharmaceutically acceptable salt thereof, to said mammal, wherein said disease or condition is selected from the group consisting of: Cushing's syndrome, gonadotropinoma, hyperparathyroidism, Paget's disease, VIPoma, nesidioblastosis, hyperinsulinism, gastrinoma, Zollinger-Ellison syndrome, irritable bowel syndrome, pancreatitis, Crohn's disease, systemic sclerosis, thyroid cancer, psoriasis, hypotension, panic attacks, sclerodoma, small bowel obstruction, gastroesophageal reflux, Graves' disease, polycystic ovary disease, upper gastrointestinal bleeding, pancreatic pseudocysts, pancreatic ascites, leukemia, meningioma, cancer cachexia, acromegaly, restenosis, hepatoma, lung cancer, melanoma, tumor, treating insulin resistance, Syndrome X, fibrosis, hyperlipidemia, hyperamylinemia, hyperprolactinemia, prolactinomas, diabetic neuropathy, macular degeneration, hypercalcemia of malignancy, and postprandial portal hypertension.

* * * * *